(12) United States Patent
Kawaguchi et al.

(10) Patent No.: US 9,465,563 B2
(45) Date of Patent: Oct. 11, 2016

(54) METHOD FOR DEFECT DETECTION IN A PRINTING SYSTEM AND PRINTING SYSTEM

(71) Applicant: OCÉ-TECHNOLOGIES B.V., Venlo (NL)

(72) Inventors: Daisuke Kawaguchi, Venlo (NL); Catharinus Van Acquoij, Venlo (NL); Ernest J. J. Clevers, Venlo (NL); Petrus L. J. Oteman, Venlo (NL)

(73) Assignee: OCE-TECHNOLOGIES B.V., Venlo (NL)

( * ) Notice: Subject to any disclaimer, the term of this patent is extended or adjusted under 35 U.S.C. 154(b) by 0 days.

(21) Appl. No.: 14/877,285

(22) Filed: Oct. 7, 2015

(65) Prior Publication Data

US 2016/0103632 A1    Apr. 14, 2016

(30) Foreign Application Priority Data

Oct. 8, 2014  (EP) .................................... 14188117

(51) Int. Cl.
*B41J 11/00*        (2006.01)
*G06F 3/12*         (2006.01)
(Continued)

(52) U.S. Cl.
CPC .................. *G06F 3/121* (2013.01); *B41J 3/60* (2013.01); *B41J 11/0095* (2013.01); *B41J 29/38* (2013.01); *B65H 7/02* (2013.01); *G01N 21/86* (2013.01); *G03G 15/5029* (2013.01); *G03G 15/55* (2013.01); *G06F 3/1234* (2013.01); *G06K 15/16* (2013.01); *G06T 7/0004* (2013.01); *H04N 1/00092* (2013.01); *H04N 1/00633* (2013.01)

(58) Field of Classification Search
CPC ... B41J 11/007; B41J 11/009; B41J 11/0095; B41J 11/42; B41J 3/60; G03G 2215/00662; G03G 2215/00704; G03G 2215/00717; B65H 2511/17; B65H 2511/135; B65H 29/60; B65H 29/62
USPC ............ 347/16, 101, 104; 271/3.17, 4.06, 6, 271/225, 227
See application file for complete search history.

(56) References Cited

U.S. PATENT DOCUMENTS 6,259,888 B1 * 7/2001 Kazama ................. B65H 29/12
                                              271/183
7,048,272 B2 * 5/2006 Lay ........................ B65H 29/60
                                              271/225
(Continued)

FOREIGN PATENT DOCUMENTS

EP    0 816 931 A1    1/1998
JP    10-194585 A     7/1998
(Continued)

*Primary Examiner* — Anh T. N. Vo
(74) *Attorney, Agent, or Firm* — Birch, Stewart, Kolasch & Birch, LLP

(57) ABSTRACT

The present invention provides an apparatus (20) for defect detection in a printing system (1). The apparatus (20) comprises: a sensing unit (21) having at least one first sensor device (22) for sensing a surface geometry or topology of a sheet (S) to be printed as the sheet (S) travels on a transport path (P) of the printing system (1) and for generating data (I) representative of that surface geometry or topology; and a processor device (25) for processing the data (I) from the first sensor device (22) to detect and classify deformations (D) in the surface geometry or topology of the sheet (S) based on at least one predetermined criterion, wherein the at least one predetermined criterion is adjustable or variable to suit operating conditions in the printing system (1). Further, the invention provides a corresponding method of detecting defects in a printing system (1).

19 Claims, 7 Drawing Sheets

(51) Int. Cl.
*B41J 3/60* (2006.01)
*B65H 7/02* (2006.01)
*G01N 21/86* (2006.01)
*G03G 15/00* (2006.01)
*G06T 7/00* (2006.01)
*H04N 1/00* (2006.01)
*B41J 29/38* (2006.01)
*G06K 15/16* (2006.01)

(56) References Cited

U.S. PATENT DOCUMENTS

| | | | |
|---|---|---|---|
| 7,496,413 B2 * | 2/2009 | Fan | G05B 13/042 162/198 |
| 8,454,111 B2 * | 6/2013 | Hayashi | B41J 11/007 347/14 |
| 8,538,316 B2 * | 9/2013 | Shigeno | G03G 15/652 271/188 |
| 8,542,260 B2 * | 9/2013 | Tsuchihashi | B65H 7/06 347/179 |
| 8,870,331 B2 * | 10/2014 | Mo | B41J 11/46 347/16 |
| 9,109,330 B2 * | 8/2015 | Shakespeare | D21G 9/0009 |
| 2004/0100016 A1 | 5/2004 | Lay et al. | |
| 2014/0092159 A1 | 4/2014 | de Jong et al. | |

FOREIGN PATENT DOCUMENTS

| | | |
|---|---|---|
| JP | 2001-124702 A | 5/2001 |
| WO | WO 00/68638 A1 | 11/2000 |

\* cited by examiner

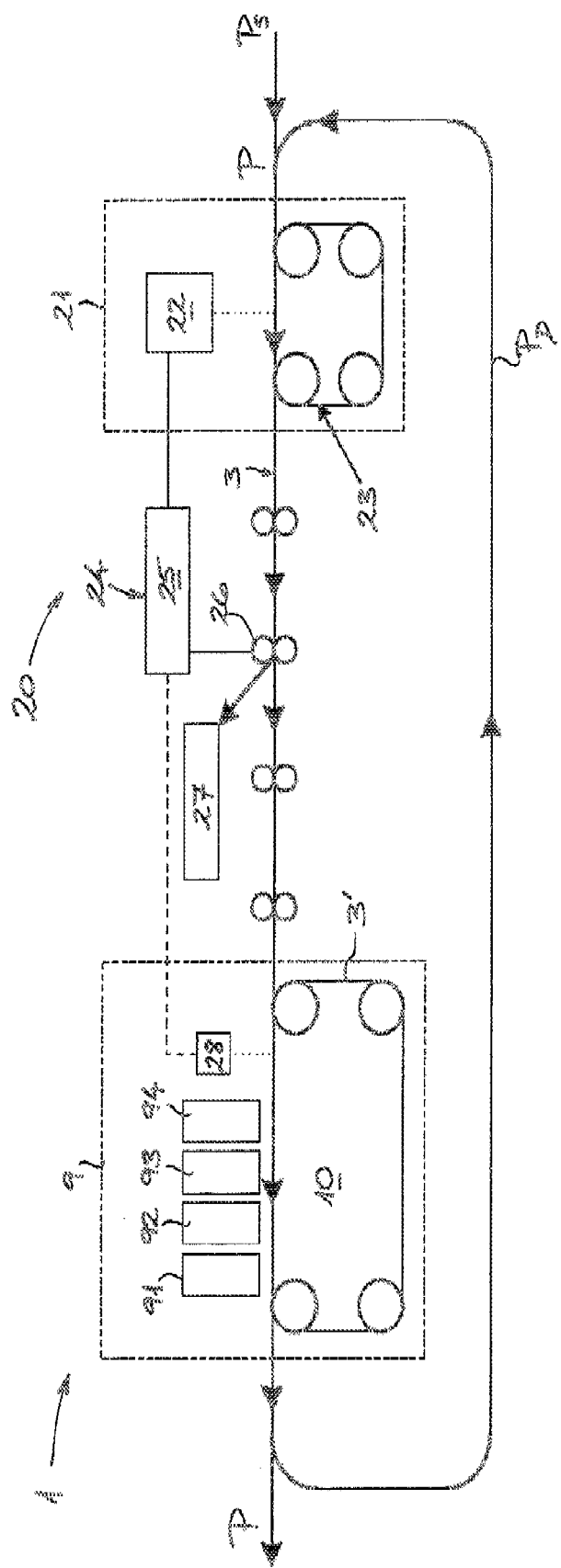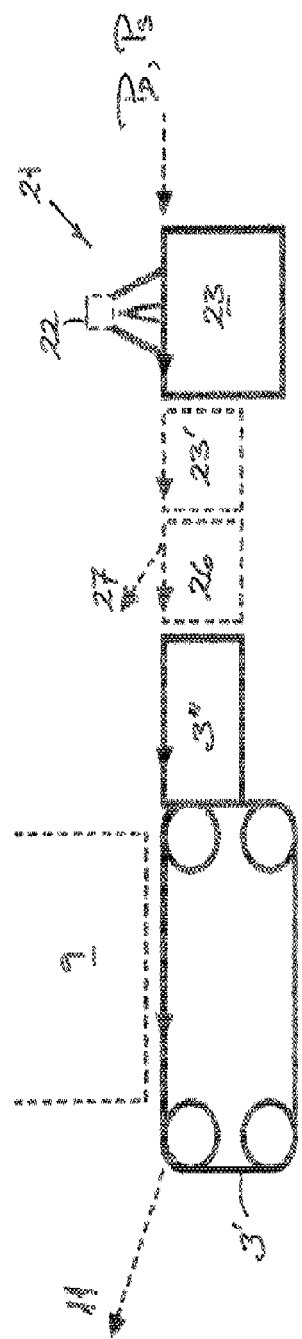
Fig. 4
Fig. 5

METHOD FOR DEFECT DETECTION IN A PRINTING SYSTEM AND PRINTING SYSTEM

FIELD OF THE INVENTION

The present invention relates to an apparatus and method for detecting a defect in a printing system, such as an inkjet printing system. The invention also relates to a printing system that includes such a defect detection apparatus to improve and/or optimize productivity and error handling of the system.

BACKGROUND OF THE INVENTION

One or more deformations present within a sheet of a medium to be printed can cause serious reliability problems in a printing system, such as an inkjet printing system, where there is only a small gap between a sheet transport mechanism and an image forming device or printing head of the printing system. If the sheet to be printed touches the image forming device or the printing head as a result of such a deformation, this can lead to print quality degradation and/or to a sheet jam in the machine. To achieve high print quality in an inkjet printing system, the distance between the printing heads and sheet to be printed should be kept small. Because of this small distance (print gap) the print heads are easily touched by the sheets as they pass. Accordingly, even small defects like dog ears, wrinkles, tears etc. can cause a so-called "head touch", which can degrade print quality, cause nozzle failure, or even sheet jams.

To address these issues, systems have been developed which employ a proofing device capable of identifying sheet deformations and rejecting sheets that contain such deformations. However, there are many sources of defects or errors that may degrade the productivity of a printing system. For example, sheets to be printed supplied to a printing machine may already contain various defects. Also, defects and wear within the machine can cause the sheets to become damaged. Changes in the environmental conditions can lead to deformation of the sheets as they are being processed, and inappropriate settings in a printing system, such as too much ink or a drying temperature that is too high, can also generate problems. Furthermore, such influences or defects can act in combination, so making it very difficult to identify a root cause of a problem.

US2004100016 A describes a media qualification device wherein sheets may be sorted among a plurality of usable media paths according to media grade. The media qualification device may further comprise an input/output device configured to select media grade parameters.

SUMMARY OF THE INVENTION

In view of the above, an object of the present invention is to provide a new and improved apparatus and method for detecting defects in a printing system, such as an inkjet printer, and a printing system or machine including such an apparatus.

It is the insight of the inventors that by selecting or adjusting the rejection criteria for a sheet in a printing system accordingly, productivity can be optimized. It is a further insight of the inventors that by adjusting rejection criteria according to a change in a job parameter, such as switching between a simplex-duplex pass or low-high productivity mode, productivity can be optimized by providing optimized criteria for each different operation condition or situation in the printing system.

According to one aspect, the invention provides a method of detecting defects in a printing system, the method comprising the steps of:

initiating a print job on the printing system based on predefined job settings, wherein the print job determines a job parameter, sensing a surface geometry of a sheet to be printed on a transport path of the sheet in the printing system to generate data representative of that surface geometry;

processing the data generated to detect deformations in the surface geometry of the sheet;

determining the suitability for printing of the sheet by comparing the data of the sheet to a reference; and selecting the reference based on the job parameter.

A print job is initiated or started by inputting the corresponding job settings for the print job into the printing system. The job settings may determine the print job and comprise, for example settings related to operating conditions, simplex/duplex information, number of sheets, colour, and/or image data. Based on the job settings, the printing system performs a set of predefined actions. For example, a sheet, which sheet has input into the printing system, is transported towards the image forming unit of the printing system. Before the sheet arrives at the image forming unit, its surface geometry is sensed by a sensing unit, which sensing unit generates data corresponding to the topology of the sheet's surface. This data is then processed by a processor device to detect out-of-plane deformations present in the sheet. Next the data of the sheet is compared to a reference to determine the suitability of the sheet for printing. A sheet not suited for printing may then be removed from the transport path to prevent it from reaching the image forming unit.

In the present invention, the reference is selectable. The reference determines when a deformation renders the sheet unsuitable for printing, and may for example provide at least one rejection criterion for the sheet. By selecting the reference, this selection criterion can be selected to be more or less strict. As such, the reference, and thereby the rejection criterion, can be selected to suit operating conditions in the printing system. In another example, the reference may be a threshold or comparison value or range.

The reference is selectable based on a job parameter of a print job. The print job determines the job parameter, which job parameter may in an example relate to a property or operating condition of the printing system. The job parameter may correspond to properties or operating conditions of the printing system. The job parameter may for example be selected or adjusted between a simplex setting wherein a sheet is on a simplex pass for printing an image on its first side and a duplex setting wherein a sheet is on a duplex pass for printing a second image on its second side. In response, the reference is selected or adjusted correspondingly, such that different rejection criteria are applied to the sheet on its duplex pass before printing the second image on its second side with respect to the same sheet on its simplex pass before printing the first image on its first side. The job parameter may further correspond to an input parameter which is comprised in or determined by the job settings. In another example, the job parameter is selectable or adjustable between a high productivity mode and a low productivity mode, respectively applying rejection criteria with different levels of strictness for rejecting sheets.

Since the reference can be selected based on a job parameter, an apparatus for defect detection is provided, which allows an operator to optimize productivity. The reference can be selected such that productivity is suitable or optimized for each set of operating conditions. Thus, a new and improved apparatus for defect detection in a printing system is provided.

In an exemplary embodiment the job settings may be arranged for determining the operating conditions of the printing system. For example, the job settings may comprise settings related to transport speed of a sheet along the transport path, simplex or duplex printing of the sheet, atmospheric conditions such as humidity and temperature, and/or productivity mode.

In a preferred embodiment, the method according to the present invention further comprises the step of determining the job parameter. The job parameter may be determined from the print job or the job settings. As such, the job parameter may be monitored at the start of the print job, continuously or intermittently. The reference is thereby selected, set or adjusted to a correct reference, allowing the proper rejection criteria to be applied.

In a further embodiment, the step of selecting the reference comprises adjusting the reference when a change in the job parameter is determined. This is particularly advantageous when the job parameter relates to an operating condition of the printing system, which condition changes through the printing process. Preferably, the job parameter is monitored and when a deviation from a previously determined job parameter state is detected, the reference is adjusted. For example, when the sheet changes from its simplex pass to its duplex pass the rejection criteria may be adjusted to be less strict.

In another embodiment, the job parameter corresponds to:
a position of a detected deformation on the sheet;
a class of a detected deformation;
whether the sheet is on a simplex pass or a duplex pass of the transport path; or
a productivity mode of the printing system.

At e.g. the leading edge a deformation present there may be a larger risk to "head touch" than compared to for example a deformation at the trailing edge. The reference is then selected or adjusted correspondingly to reject sheets with deformations in such unwanted positions of the sheet, while sheet with the same deformation in other more favourable positions on the sheet may be allowed to pass to the print head. Likely, the method may apply different rejection criteria for different deformation classes. For example, a dog ear may be unwanted and dog-eared sheets are then rejected, while sheets with minor wrinkles may be allowed to pass to the print head. Likewise, the method may apply stricter references for a sheet on its simplex pass than on its duplex pass, since after simplex printing a sheet may pass again through the print head for duplex printing. Further, the reference may be adjusted based on a productivity mode of the printing system. This allows the operator to switch between for example a high productivity and a low productivity, wherein production speed of the printing system may be increased by for example reducing quality.

In an embodiment, the invention provides a method of detecting defects in a printing system, comprising:
sensing a surface geometry or a topology of a sheet to be printed on a transport path of the sheet in the printing system to generate data representative of that surface geometry or topology;
processing the surface geometry or topology data generated to identify and classify deformations in the surface geometry or topology of the sheet according to at least one predetermined criterion;
wherein the processing step includes selecting, varying or adjusting the at least one predetermined criterion depending upon operating conditions or parameters of the printing system.

In an embodiment, the step of processing the surface geometry or topology data according to the predetermined criterion preferably includes determining whether one or more deformations identified or detected in the sheet renders the sheet unsuitable for printing. In particular, the at least one predetermined criterion will typically include one or more of: height of a detected deformation out of a plane of the sheet, and area of a detected deformation in the plane of the sheet. Thus, the step of determining the suitability of the sheet for printing comprises determining whether a deformation detected has a particular classification, e.g. a size and/or a shape classification. The method may determine that a detected deformation exceeds a reference and thus renders the sheet unsuitable for printing.

Furthermore, in a preferred embodiment the method includes controlling further progress of the sheet along the transport path of the printing system depending on the deformations identified and classified in the surface geometry or topology of the sheet. In this regard, controlling the further progress of the sheet along the transport path preferably includes controlling or effecting removal of the sheet from the transport path of the printing system if one or more deformations identified in the surface geometry or topology of the sheet would render the sheet unsuitable for printing. Thus, the method may include removing or ejecting a sheet from the transport path of the printing system if a deformation detected is determined to exceed the reference. With the present invention, the shape of each sheet is sensed or measured in real time and can be rejected according to preselected criteria, optionally depending on multiple factors, e.g. the defect height can be combined with defect area. As the method of the invention measures out-of-plane deformations, all relevant shape parameters can be used as rejection criteria. The sheets do not need to be deformed deliberately to test run-ability of the system.

In a preferred embodiment, selecting, varying or adjusting the at least one predetermined criterion can depend on one or more of: a material of the sheet to be printed, an operating mode of the printing system, a position of a detected deformation on the sheet, a shape or type of a detected deformation, and/or whether the sheet is on a simplex pass or a duplex pass of the transport path.

In a preferred embodiment, the step of sensing the surface geometry or topology of the sheet includes holding and conveying the sheet on the transport path in a manner substantially identical to a manner of holding and conveying the sheet in an image forming unit or printing head unit of the printing system. In this way, it is possible to detect and to measure or classify deformations in the surface of the sheet that may be expected in the image forming unit or printing head unit of the printing system with reasonable accuracy. That is, the detection and measurement of sheet deformations is highly dependent on the transport conditions. Thus, by using simulated transport conditions, with the possibility to adapt one or more of the relevant parameters, the method of the invention allows accurate prediction or assessment of the sheet deformation at the image forming unit.

As also discussed above, the printing process may comprise a single-pass of the print medium sheets through an image forming unit or, alternatively, a multi-pass process for image formation. In a preferred embodiment, the step of sensing the surface geometry or topology of the sheet takes place on a first pass or simplex pass of the sheet on the transport path towards an image forming unit or a printing head unit of the printing system. In a multi-pass (e.g. duplex) printing process, the step of sensing the surface geometry or topology of the sheet preferably takes place on each pass of the transport path by a sheet of print medium towards the image forming device or printing head unit of the printing system. In this regard, the sensing step preferably includes sensing the surface geometry or topology of substantially an entire surface or side of the sheet. This sensing operation may, for example, be performed by an optical sensor or scanner, such as a laser scanner. Thus, the surface geometry data or topology data will typically include image data comprising image elements or pixels.

In a preferred embodiment, the processing step comprises applying at least one algorithm to the surface area or topology data. The at least one algorithm may be configured to analyse pixels of the data row-by-row (or by row major) according to at least one criterion, such as height, to identify and classify deformations in the sheet. In this context, the algorithm preferably analyses neighbouring pixels of a pixel detected within a deformation.

According to another aspect, the invention provides a printing system arranged for performing a print job based on predefined job settings, comprising an apparatus for defect detection, which apparatus comprises:
  a sensing unit comprising a first sensor device for sensing a surface geometry of a sheet to be printed as the sheet travels on a transport path of the printing system and for generating data representative of that surface geometry;
  a processor device for processing the data from the first sensor device configured to detect deformations in the sheet and to determine whether a detected deformation renders the sheet unsuitable for printing by comparing a detected deformation to a reference;
  a controller for selecting the reference based on a job parameter determined by the print job.

By inputting job settings into the printing system, a print is started or performed. After a sheet is input into an apparatus according to the present invention, the sheet is sensed by the sensing unit to determine the surface geometry or topology of the sheet's surface. The sensing unit may in an embodiment measure a height map of the sheet surface, which height is then converted into data and sent to the processor device. The processor device may then analyze the data to determine whether deformations are present in the sheet, for example by scanning for irregularities in the height map. When a deformation is detected, the processor device determines whether the detected deformation renders the sheet unsuitable for printing. Thereto, the processor device compares the detected deformation to a reference. The data related to the detected deformation is compared to the reference. The processor device may determine at least one property of the detected deformation, for example the maximum height. The processor may then check whether this determined property exceeds the reference, and based on that, identify the sheet as unsuitable for printing.

The reference is selectable by means of a controller. The reference preferably defines rejection criteria which determine when a sheet is deemed unsuitable for printing. The reference may comprise a reference value related to determined properties of the detected deformation. A threshold or threshold size may be provided by the reference against which the properties of the deformations in the sheet may be compared. In a basic example, the reference is the print head gap spacing and any sheet wherein a deformation with a maximum height exceeding the print head gap spacing is detected, is deemed unsuitable for printing, and may be subsequently ejected from transport path of the printing system.

The reference is selectable based on a job parameter determined by the print job. The job settings of the print job may for example relate to the operating conditions or properties of the printing systems during the execution of the print job. As such, the job settings define the operating conditions to which the sheet is exposed to while in the printing system.

The job parameter preferably relates to at least one operation condition of the printing system operation during operation. As such, the job parameter may reflect the state of the sheet during operation, for example the sheet transport velocity, the sheet position in the printing system (e.g. on a simplex or a duplex pass), the sheet's printing condition (i.e. unprinted, one-sided printed, or two-sided printed). The job parameter preferably automatically triggers the selection or adjustment of the reference. In a basic example, the reference is adjustable by the controller from a first predefined reference setting to a second predefined reference upon detection of a change in the job parameter. Thereto, the controller may be arranged for detecting a change in or adjustment of the job parameter.

When operating conditions remain the same, there is no need to adjust preferably previously optimized references and thereby the corresponding rejection criteria. When the operating conditions change, for example between simplex and duplex passes, a reference for a rejection criterion may be adjusted accordingly. The change in operating conditions may be determined from a change in a job parameter, which may be monitored by the processor device. When the operating conditions change, for example by input from the operator or a change to the operating conditions of the sheet in the printing system, the processor device may detect this change and select or adjust the reference according to predetermined instructions. For example, when the operator selects a "high productivity" mode on a user interface, the processor device instructs the controller to accordingly increase the relevant references. Thereby, the manual selection or adjustment of the thresholds is eliminated, increasing productivity.

In another embodiment, the controller and/or processor device is arranged to determine a change in the at least one job parameter. The job parameter may be an input parameter, such as the setting for high or low productivity mode. Such input parameters may in an example be selected or adjusted by an operator via a user interface. Other job parameters may relate operating conditions of the printing system, operating conditions of the sheet in the printing system and/or to deformations on the sheet, and may be monitored via the sensing unit, processor device or controller. These operating conditions may be monitored by the apparatus and/or printing system, such that any change is determined automatically and requires no manual adjustment of an operator. Such job parameters may for example be, a position of a detected deformation on the sheet, a type or class of a detected deformation on the sheet, the sheet being transported on a simplex or duplex pass, and/or detected sheet size.

In an embodiment, the reference determines a threshold value for a height of a deformation out of a plane of the sheet, and/or an area of a deformation in the plane of the sheet. The reference may define an upper limit, lower limit and/or a range for at least one property determined by the processor device from the data. Preferably, the processor device determine whether at least one property of at least one detected deformation lies within at least one range corresponding to the reference for said at least one property to determine whether a sheet is suitable for printing. For example, the maximum height of each detected deformation may be compared to an upper height limit, such as the print head gap spacing to avoid "head touch".

In a further embodiment, the at least one job parameter comprises information related to an operating mode of the printing system, a position of a deformation on the sheet, a shape or type of a deformation, and/or whether the sheet is on a simplex pass or a duplex pass of the transport path. The controller may select or adjust the reference according to predefined instructions when the operating conditions and/or a corresponding job parameter change. The job parameter may in another example correspond to a high productivity mode and a low productivity mode, wherein the rejection criteria for the latter are stricter than for the first. In a further example, the processor device determines the position of a deformation on the sheet and transmits this data to the controller, which may apply certain stricter criteria when said deformation is located near or on the leading edge of the sheet in comparison to criteria applied when a deformation is located at the trailing edge. By monitoring the relevant job parameter, the apparatus according to the present invention can compensate swiftly for any change in the printing process.

In another embodiment, an input module is provided which comprises a user interface and/or a memory unit for storing job parameters and/or print job settings. The memory unit may further store instructions for selecting or adjusting the reference. Via the user interface the operator may input the job settings for the print job. Further, the user may for example change the operating conditions and/or job parameter settings or instructions, whereupon the controller adjusts the reference according to the instructions stored on the memory unit. The print job setting may comprise values or ranges for references.

In an embodiment the controller is arranged for selecting or adjusting the reference for determining whether a detected deformation renders the sheet unsuitable for printing between at least two threshold values based on the at least one job parameter of the input module. The controller is arranged to adjust a reference from one of the at least two threshold values to the other of the at least two threshold values when a relevant job parameter is changed. Preferably, a plurality of reference values is defined for each reference, wherein each threshold value corresponds to a value of an job parameter. For example, when the job parameter changes from value A to B, the reference for maximum sheet height is changed from value A' to B', and the reference for maximum area is changed from A" to B".

In an embodiment, the controller is arranged for determining the job parameter, for example by continuously or intermittently monitoring the job parameter. In a preferred embodiment, the controller is arranged for adjusting the reference when a change in the job parameter is determined, for example when a productivity mode is adjusted from low productivity mode to high productivity mode. In a further embodiment, the controller is arranged for selecting or adjusting the reference between at least two reference values. The reference values may be stored on a memory of the controller or printing system. As such, the printing system may switch between predefined reference based upon changes in the properties or operating conditions of the printing system.

In an embodiment. the at least one job parameter corresponds to:

a position of a detected deformation on the sheet;
a class of a detected deformation;
whether the sheet is on a simplex pass or a duplex pass of the transport path; or
a productivity mode of the printing system.

In a further embodiment, the apparatus according to the present invention further comprises a controller for controlling further progress of the sheet along the transport path of the printing system depending on deformations in the surface geometry or topology of the sheet detected and classified by the processor device, wherein the controller is configured to control and/or operate a removal device for removing the sheet from the transport path of the printing system if the processor device detects one or more deformations in the surface geometry or topology of the sheet that would render the sheet unsuitable for printing; the apparatus preferably including said removal device.

In another embodiment, the sensor unit is configured and arranged to sense the surface geometry or topology of the sheet when the sheet is on a first pass or simplex pass of the transport path towards an image forming unit or a printing head unit of the printing system; and/or wherein the sensing unit is configured and arranged to sense the surface geometry or topology of the sheet when the sheet is on a second pass or a duplex pass of the transport path towards the image forming or printing head unit of the printing system. The sensing unit preferably includes a conveyor mechanism which is configured to hold and transport the sheet on the transport path in a manner substantially identical to a transport mechanism in an image forming unit or printing head unit of the printing system.

In an embodiment, the present invention provides an apparatus for detecting a defect in a printing system according to the present invention, which apparatus comprises: a sensing unit comprising a first sensor device for sensing a surface geometry of a sheet to be printed as the sheet travels on a transport path of the printing system and for generating data representative of that surface geometry;
a processor device for processing the data from the first sensor device configured to detect deformations in the sheet and to determine whether a detected deformation renders the sheet unsuitable for printing by comparing a detected deformation to a reference;
a controller for selecting the reference based on a job parameter determined by the print job.

In this way, the invention provides a printing system with an apparatus or device for sheet deformation measurement which is capable of sensing and measuring the surface shape of the sheet. By analysing the surface shape data of the sheet, relevant deformations or defects in the sheet and their properties can be detected or identified or extracted from the data. Furthermore, a classification can be made for each deformation or defect found within the sheet; for example, a type or shape classification (e.g. a "dog ear", curl, or waviness) and/or a size classification can be made. The data from the detection and classification of the deformations may then be used to assess or determine the suitability of the sheet for printing, to find a root cause or root defect in the printing system and/or to monitor printing system performance. Because the impact of a deformation or defect in a sheet on the printing system may vary depending on a range of different operating parameters or conditions in the system, the present invention is designed to modify or vary the at least one predetermined criterion depending on those operating parameters or conditions. The processor device will typically include a data storage unit for storing the data from the at least one first sensor device as well as the predetermined criteria. As explained above, the reference may be selected or adjusted by the controller based upon a job parameter determined by the print job to provide an accurate and versatile system.

In an embodiment, the present invention provides an apparatus for detecting a defect in a printing system, comprising:

a sensing unit comprising at least one first sensor device for sensing a surface geometry or topology of a sheet to be printed as the sheet travels on a transport path of the printing system and for generating data representative of that surface geometry or topology; and a processor device for processing the data from the first sensor device to detect and classify deformations in the surface geometry or topology of the sheet based on at least one predetermined criterion. The at least one predetermined criterion is selectable, adjustable or variable to suit operating conditions in the printing system.

In a preferred embodiment of the invention, the processor device is configured to detect and classify deformations in the surface geometry or topology of the sheet to determine whether a deformation renders the sheet unsuitable for printing; for example, because a detected deformation exceeds a reference or extent. The at least one predetermined criterion therefore preferably includes one or more of: a height of a deformation out of a plane of the sheet, and an area of a deformation in the plane of the sheet. In the event that the sheets have a defect, such as a curl, waviness or a dog-ear, these sheets increase the risks of a sheet jam, damage to the image forming unit or printing head, defects in the printed image, and so on. Therefore, the apparatus is designed to avoid such potential risks to increase the printing system productivity, lifetime, and print quality. Sheet deformation can often arise when loading the sheet into the printing system. By applying the at least one predetermined criterion for assessing the sheets on a first or single pass of the transport path, it is possible to supply only non-damaged or non-defective sheets to image forming unit, so that the above-mentioned risks can be minimized.

In a preferred embodiment, the apparatus includes a controller which controls further progress of the sheet on the transport path of the printing system depending upon the deformations in the surface geometry or topology of the sheet detected by the processor. The controller is configured to control and/or to operate a removal device for removing the sheet from the transport path of the printing system if and when the processor device identifies one or more deformations in the surface geometry or topology of the sheet that render the sheet unsuitable for printing. In this way, the invention is configured to prevent the printing system from being stopped or negatively impacted by a defective print medium sheet. When a sheet deformation or defect is found, the sheet can be removed from the transport path, e.g. via a removal device or ejector device that may switch or re-route the defective sheet to a reject tray. Such a removal device or ejector device operated by the controller is preferably part of the apparatus of the invention. Depending on the result of sheet form sensing, therefore, every sheet is assessed or analysed according to the at least one predetermined criterion (i.e. as a removal or ejection criterion) as to whether the sheet should be removed or ejected from the transport path. The removal or ejection criterion is typically defined in terms of a maximum or threshold height out of the plane of the sheet. If the sheet has higher defect than a given threshold value, the sheet will be removed or ejected.

In other words, to prevent the printing system from experiencing a loss of print quality, or a nozzle failure or a sheet jam, the controller can operate to prevent a sheet in which one or more deformations or defects are detected from progressing to an image forming device or printing head unit of the system. Especially humidity problems and wear of the system will show a gradual defect build up. Preventive measures can be taken to maintain system performance. As the apparatus of the invention employs data representative of the surface geometry or topology of the sheet (e.g. three-dimensional data), the invention is capable of detecting multiple deformation types. Thus, any relevant deformation present within the sheet can be detected using a full sheet topology measurement, e.g. a 3D image of the sheet surface. On the other hand, if the apparatus determines a sheet to be free of deformations or defects or to have only tolerable deformations or defects, it is allowed to progress to the image forming unit.

The printing system may be designed for a single-pass of the print medium sheets through an image forming device or for multi-pass image formation. In a preferred embodiment, the sensor device of the apparatus is configured and arranged to sense the surface geometry or topology of the sheet when the sheet is on a first pass or simplex pass of the transport path towards an image forming device or a printing head unit of the printing system. In the event the printing system employs multi-pass image formation, the sensor device of the apparatus may be configured and arranged to sense the surface geometry or topology of the sheet each time the sheet makes a pass of the transport path towards the image forming device or printing head unit of the printing system. For example, in a duplex-pass printing system, the sensor device is configured and arranged to sense a surface geometry or topology of the sheet both on the first pass or simplex pass as well as on the second pass or duplex pass.

The moment in time at which a sheet deformation or defect appears within the printing process and the shape and/or the size of the deformation or defect can help to determine the cause of that defect. For example, if a pack of paper print medium sheets is dropped before being fed into a printing system, the associated defects in the paper will appear directly at a simplex pass proofing. In such a case, where a sheet is identified as having a dog-eared corner, it is highly probable that many subsequent sheets will also have a dog ear at one of the corners of the sheet. It will be appreciated, however, that the sheets to be printed can also be damaged or acquire one or more defects during the printing process on a simplex pass through the system. For example, sheets can develop very specific waviness deformations due to humidity variation that can readily be distinguished from dog ears and curl defects. On the other hand, if the duplex sheet transport mechanism in the printing system is defective, the sheets may become damaged during the duplex pass. In such a case, the presence of a defect in the duplex pass may be confirmed by the simplex pass sheet analysis showing that the sheet was not damaged at that time. For this reason, sheet form sensing on the duplex pass also helps to decrease the above-mentioned risks of sheet jam, damage to the image forming unit or printing head, defects in the printed image, and so on. Significantly, however, the impact of removing or rejecting a sheet on the duplex pass can be higher than removing or rejecting a sheet on the simplex pass. Because sheet removal on the duplex pass results in a missing page in the output, duplex sheets following a removed or rejected sheet also need to be removed to ensure that the printed images are in a correct order in the final output stock. Due to this fact, the impact of sheet removal on productivity is multiplied in the duplex pass. If a user prefers higher productivity, sheets should be removed or rejected as little as possible on the duplex pass, to the extent that this does not cause serious problems. Such different requirements or criteria for removal or ejection between the simplex and the duplex passes of the transport path may, for example, be satisfied by setting a larger threshold value for a removal or ejection criterion in the duplex pass than in the simplex pass.

In a particularly preferred embodiment, therefore, the at least one predetermined criterion is selectable, adjustable or variable depending upon one or more of: a material of the sheet to be printed, an operating mode of the printing system, a position of a deformation on the sheet, a shape or type of a deformation, and/or whether the sheet is on a simplex pass or a duplex pass of the transport path. Because the likelihood of sheet damage or deformation occurring on the duplex pass typically depends on the material or print medium of the sheet, it is possible to set a unique simplex and duplex threshold for each material or print medium type. Furthermore, it is possible that the printing system has different modes of operation, such as a productivity mode or a print-quality mode, each of which may then have different removal or ejection criteria. In addition, it is possible to vary the predetermined criterion based on defect location within the sheet or based on the type of defect. In this regard, it will be noted that a higher threshold value for trailing edge defects and/or for waviness on a side edge may be provided or tolerated because these are less likely to cause a sheet jam.

As it is desired to prevent defective sheets from reaching the printing heads of an image forming unit in the printing system, the removal device is typically arranged to remove the sheet from the transport path upstream of the image forming unit or printing head unit of the system. To this end, the sensing unit should be spaced a sufficient distance from the image forming unit; i.e. space is required to remove a sheet containing deformations from the transport path. The sensing unit may therefore be provided as a "sentry unit" for location in the transport path of the printing system before (i.e. upstream of) the image forming unit to allow the removal device or ejector device to be positioned between the sentry unit and the image forming unit. The minimum distance along the transport path between the sentry unit and the image forming unit may be determined by a sheet length and the processing time needed to detect and classify deformations. For example, a long sheet could have a defect on the trailing edge. The processor device will require time to process the data generated by the first sensor device and detect a deformation at the trailing edge after this has passed the measurement position. Thus, a leading edge of the sheet should not have passed the removal device at the moment of sensing the trailing edge of the sheet in order to ensure that a removal of the sheet upstream of the image forming unit is still possible. In this regard, a sheet transport mechanism for transporting or conveying the sheets to be printed between the sentry unit and the image forming unit may be different to a transport mechanism employed by each of the sensing unit and the image forming unit. Specifically, this sheet transport mechanism in between may be optimized for a reliable sheet removal or ejection.

In a preferred embodiment of the invention, the sensing unit includes a conveyor mechanism which is configured to hold and transport the sheet on the transport path in a manner substantially identical to a transport mechanism in an image forming unit or printing head unit of the printing system. In particular, to be able to obtain an accurate measurement at the sensing unit, the sheet surface should be transported under substantially identical conditions as when it is transported at the image forming unit. The sheet transport mechanism within the sensing unit thus simulates transport conditions used within the image forming unit. This way, the deformations measured within the sensing unit can be used to accurately predict the deformations that will be present within the sheet at the image forming unit. Simulated transport conditions can be obtained by using a functionally identical suction belt conveyor within the sensing unit if the image forming unit also uses a suction belt conveyor as sheet transport mechanism. To create the same vacuum hold down force it is not only important that the vacuum force (or under-pressure) is substantially identical for both belt conveyors, but also the suction hole diameter and pattern, the geometry of the vacuum forming channels within the belt support structure, etc. The same applies for other sheet conveyor means; e.g. with one or more gripper members within the sensing unit if the image forming unit also has one or more gripper members. In addition, means may be provided for adjusting relevant sheet transport condition parameters in the conveyor mechanism of the sensing unit for greater accuracy in simulating sheet transport conditions at image forming unit.

In a particularly preferred embodiment, the sheet to be printed is a sheet of a print medium selected from the group comprised of: paper, polymer film, such as polyethylene (PE) film, polypropylene (PP) film, polyethylene terephthalate (PET) film, metallic foil, or a combination of two or more thereof.

In a preferred embodiment of the invention, the processor device is configured to detect and classify deformations in the surface geometry or topology of the sheet to determine whether a deformation identified exceeds a reference to thereby render the sheet unsuitable for printing. Alternatively, or in addition, the processor device is configured to detect and classify deformations in the surface of the sheet for statistical purposes to determine print media reliability. In this regard, the data is analysed by the processor device to determine any one or more of: a number of deformations present within a sheet, a height of each deformation, and area of each deformation. In this way, the apparatus for sheet topology measurement and defect detection and classification may also be used to create test methods for determining the run-ability of print media and optimizing the print and processing parameters depending on the medium used; e.g. the maximum ink coverage that can be used on a certain medium type.

In a preferred embodiment, the sensor device is configured and arranged to sense the surface geometry or topology of the sheet when the sheet is on a transport path of the printing system. As noted above, the apparatus may include an ejector device for removing the sheet from the transport path of the printing system if the processor device determines that the sheet is unsuitable for printing. In this case, a sheet may be determined as unsuitable for printing if, for example, a deformation detected has a particular shape classification (e.g. a "dog ear", curl, or waviness) and/or a particular size classification (e.g. if the deformation detected exceeds a reference, such as a maximum allowable height and/or a maximum allowable area). The controller is configured to control the ejector device to remove the sheet from the transport path depending on the processing of the surface geometry or topology data by the processor. The apparatus for measuring sheet deformation is thus used for rejecting sheets from the paper path to enhance printing reliability.

In a particularly preferred embodiment, the apparatus further comprises at least one second sensor device located downstream of the first sensor device, and typically upstream of and/or in an image forming unit or printing head unit of the printing system, for sensing a surface geometry or a topology of a sheet to provide feedback data or correlation data to the processor device for comparison with the data from the at least one first sensor device. As will be appreciated, the sheet transport conditions can never be reproduced with one-hundred percent accuracy at the sensing unit and this limits the accuracy of the sheet deformation analysis or measurement by the apparatus. By adding a second sheet shape measurement or sensor device at the image forming unit, the accuracy can be tested and improved by using feedback. The second sensor device or measuring device at the image forming unit does not necessarily have to be identical to the first sensor device. A more limited system, e.g. a single point measurement device, could be used to provide feedback for a two-dimensional (2D) profile measuring device.

In a preferred embodiment, either or both of the first and second sensor devices is configured to sense substantially an entire surface or side of the sheet, preferably via an optical sensor, such as a laser scanner. In this way, the surface geometry or topology data typically includes image data comprising pixels. The processor device is preferably configured to detect and classify deformations in the surface geometry or topology of the sheet according to at least one of a plurality of criteria including: height (e.g. in mm), area (e.g. in pixels), bounding area (e.g. in pixels), and/or centre of gravity in the surface geometry or topology data processed. To this end, the processor device typically employs at least one algorithm for processing or analysing the surface area or topology data from the sensor device. In particular, a reliable deformation or defect classification which is independent of the defect size and shape can be accomplished by a recognition algorithm using defect property parameters that are independent of the type of deformation. These preferably include: a bounding box (e.g. in the form of a rectangular box drawn around and entirely encompassing the deformation in the data), an area of the defect or deformation, centre of gravity, and maximum height and position of the defect or deformation.

In a particularly preferred embodiment, the at least one algorithm is configured to analyse an array of pixels in the surface geometry or topology data (image data) row-by-row according to at least one criterion, such as height, to identify and to classify a deformation in the sheet. Further, the algorithm may be configured to analyse neighbouring pixels of a pixel within a deformation.

A classification algorithm for classifying a detected defect or deformation in the present invention typically uses simple-to-calculate properties like a bounding box (e.g. a rectangular box drawn around and encompassing the deformation), an area of the deformation, a centre of gravity of the defect or deformation, and maximum height and position of the defect or deformation. These properties are generally easy to calculate in real time. The dog-ear type of defect or deformation has a unique property that the maximum height is located at the corner of the bounding box, which is located at the corner of the sheet. The maximum height of a wave type of defect or deformation is located in the middle of one of the vertices of the bounding box, which in turn is located at one of the edges of the sheet. It will be appreciated that other algorithms, e.g. employing correlation techniques, can also be used but these may be much more computation intensive and sensitive to the actual defect shape and size.

BRIEF DESCRIPTION OF THE DRAWINGS

For a more complete understanding of the invention and the advantages thereof, exemplary embodiments of the invention are explained in more detail in the following description with reference to the accompanying drawing figures, in which like reference characters designate like parts and in which:

FIG. 4 is a schematic side view of a printing system with a defect detection system according to an embodiment of the invention;

FIG. 5 is a schematic side view showing more detail of a printing system with a defect detection system in the duplex transport path according to an embodiment of the invention;

The accompanying drawings are included to provide a further understanding of the present invention and are incorporated in and constitute a part of this specification. The drawings illustrate particular embodiments of the invention and together with the description serve to explain the principles of the invention. Other embodiments of the invention and many of the attendant advantages of the invention will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will further be appreciated that certain actions and/or steps in an embodiment of a method may be described or depicted in a particular order of occurrences while those skilled in the art will understand that such specificity with respect to sequence is not actually required. It will also be understood that the terms and expressions used in the present specification have the ordinary meaning as is accorded to such terms and expressions with respect to their corresponding respective areas of inquiry and study, except where specific meanings have otherwise been set forth herein.

DETAILED DESCRIPTION OF EMBODIMENTS

Figure 1:
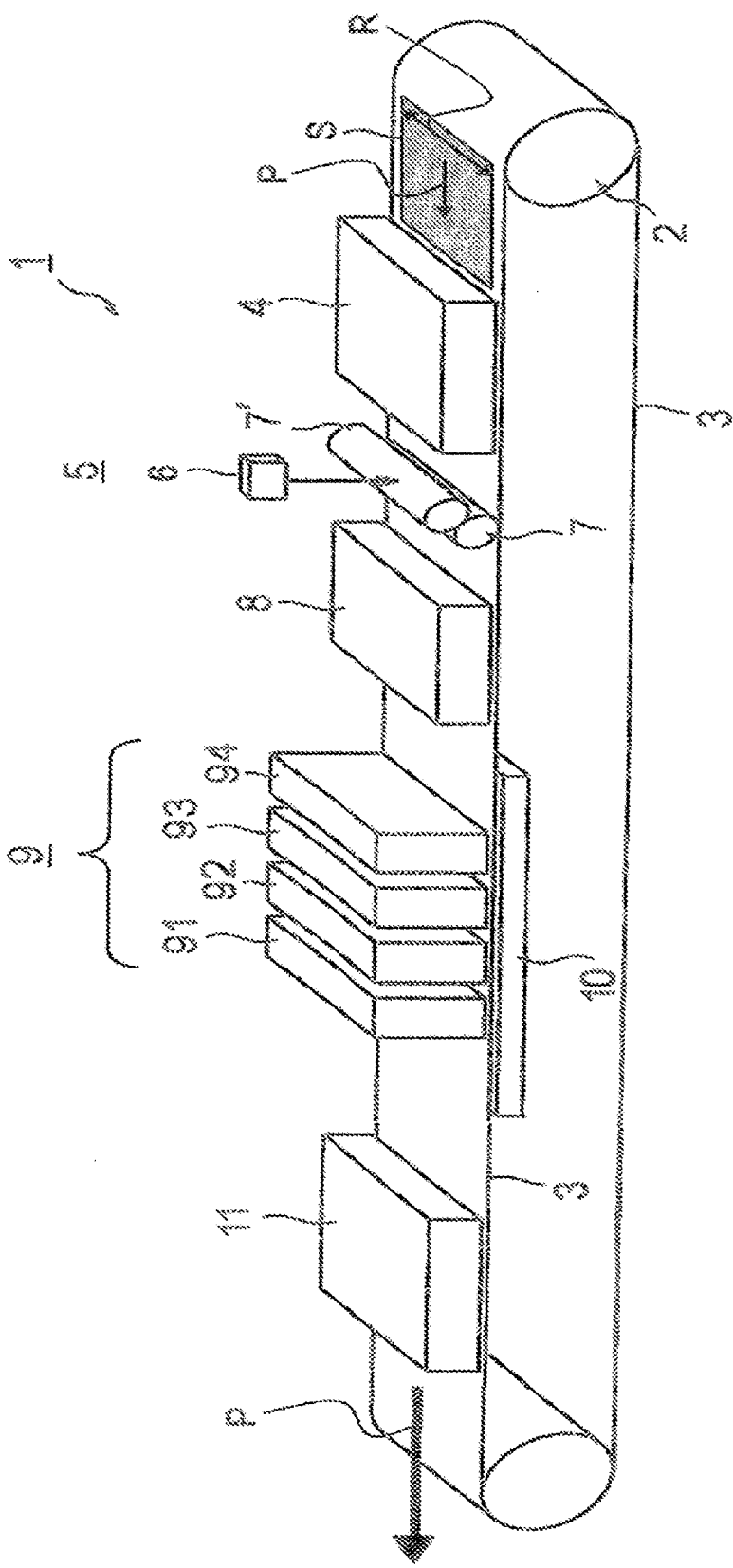
FIG. 1 is a schematic side view of part of a printing system according to an embodiment of the invention.

With reference to FIG. 1 of the drawings, a portion of an inkjet printing system 1 according to a preferred embodiment of the invention is shown. FIG. 1 illustrates in particular the following parts or steps of the printing process in the inkjet printing system 1: media pre-treatment, image formation, drying and fixing and optionally post treatment. Each of these will be discussed briefly below.

FIG. 1 shows that a sheet S of a receiving medium or print medium, in particular a machine-coated print medium, is transported or conveyed along a transport path P of the system 1 with the aid of transport mechanism 2 in a direction indicated by arrows P. The transport mechanism 2 may comprise a driven belt system having one or more endless belt 3. Alternatively, the belt(s) 3 may be exchanged for one or more drums. The transport mechanism 2 may be suitably configured depending on the requirements of the sheet transport in each step of the printing process (e.g. sheet registration accuracy) and may hence comprise multiple driven belts 3, 3' and/or multiple drums. For a proper conveyance of the sheets S of the receiving medium or print medium, the sheets S should be fixed to or held by the transport mechanism 2. The manner of such fixation is not limited and may, for example, be selected from the group: electrostatic fixation, mechanical fixation (e.g. clamping) and vacuum fixation, of which vacuum fixation is particularly preferred.

Media Pre-Treatment

To improve spreading and pinning (i.e. fixation of pigments and water-dispersed polymer particles) of the ink on the print medium, in particular on slow absorbing media, such as machine-coated media, the print medium may be pre-treated, i.e. treated prior to the printing of an image on the medium. The pre-treatment step may comprise one or more of the following:

(i) pre-heating of the print medium to enhance spreading of the ink used on the print medium and/or to enhance absorption into the print medium of the ink used;
(ii) primer pre-treatment for increasing the surface tension of print medium in order to improve the wettability of the print medium by the ink used and to control the stability of the dispersed solid fraction of the ink composition, i.e. pigments and dispersed polymer particles; (N.B. primer pre-treatment can be performed in a gas phase, e.g. with gaseous acids such as hydrochloric acid, sulphuric acid, acetic acid, phosphoric acid and lactic acid, or in a liquid phase by coating the print medium with a pre-treatment liquid. A pre-treatment liquid may include water as a solvent, one or more co-solvents, additives such as surfactants, and at least one compound selected from a polyvalent metal salt, an acid and a cationic resin); and
(iii) corona or plasma treatment.

FIG. 1 illustrates that the sheet S of print medium may be conveyed to and passed through a first pre-treatment module 4, which module may comprise a preheater, (e.g. a radiation heater), a corona/plasma treatment unit, a gaseous acid treatment unit or a combination of any of these. Subsequently, a predetermined quantity of the pre-treatment liquid may optionally be applied on a surface of the print medium via a pre-treatment liquid applying device 5. Specifically, the pre-treatment liquid is provided from a storage tank 6 to the pre-treatment liquid applying device 5, which comprises double rollers 7, 7'. A surface of the double rollers 7, 7' may be covered with a porous material, such as sponge. After providing the pre-treatment liquid to auxiliary roller 7' first, the pre-treatment liquid is transferred to main roller 7, and a predetermined quantity is applied onto the surface of the print medium. Thereafter, the coated printing medium (e.g. paper) onto which the pre-treatment liquid was applied may optionally be heated and dried by a dryer device 8, which comprises a dryer heater installed at a position downstream of the pre-treatment liquid applying device 5 in order to reduce the quantity of water content in the pre-treatment liquid to a predetermined range. It is preferable to decrease the water content in an amount of 1.0 weight % to 30 weight % based on the total water content in the pre-treatment liquid provided on the print medium sheet S. To prevent the transport mechanism 2 from being contaminated with pre-treatment liquid, a cleaning unit (not shown) may be installed and/or the transport mechanism 2 may include a plurality of belts or drums 3, 3', as noted above. The latter measure avoids or prevents contamination of other parts of the printing system 1, particularly of the transport mechanism 2 in the printing region.

It will be appreciated that any conventionally known methods can be used to apply the pre-treatment liquid. Specific examples of an application technique include: roller coating (as shown), ink-jet application, curtain coating and spray coating. There is no specific restriction in the number of times the pre-treatment liquid may be applied. It may be applied just one time, or it may be applied two times or more. An application twice or more may be preferable, as cockling of the coated print medium can be prevented and the film formed by the surface pre-treatment liquid will produce a uniform dry surface with no wrinkles after application twice or more. A coating device 5 that employs one or more rollers 7, 7' is desirable because this technique does not need to take ejection properties into consideration and it can apply the pre-treatment liquid homogeneously to a print medium. In addition, the amount of the pre-treatment liquid applied with a roller or with other means can be suitably adjusted by controlling one or more of: the physical properties of the pre-treatment liquid, the contact pressure of the roller, and the rotational speed of the roller in the coating device. An application area of the pre-treatment liquid may be only that portion of the sheet S to be printed, or an entire surface of a print portion and/or a non-print portion. However, when the pre-treatment liquid is applied only to a print portion, unevenness may occur between the application area and a non-application area caused by swelling of cellulose contained in coated printing paper with water from the pre-treatment liquid followed by drying. From a view-point of uniform drying, it is thus preferable to apply a pre-treatment liquid to the entire surface of a coated printing paper, and roller coating can be preferably used as a coating method to the whole surface. The pre-treatment liquid may be an aqueous liquid.

Corona or plasma treatment may be used as a pre-treatment step by exposing a sheet of a print medium to corona discharge or plasma treatment. In particular, when used on media such as polyethylene (PE) films, polypropylene (PP) films, polyethylene terephthalate (PET) films and machine coated media, the adhesion and spreading of the ink can be improved by increasing the surface energy of the medium. With machine-coated media, the absorption of water can be promoted which may induce faster fixation of the image and less puddling on the print medium. Surface properties of the print medium may be tuned by using different gases or gas mixtures as medium in the corona or plasma treatment. Examples of such gases include: air, oxygen, nitrogen, carbon dioxide, methane, fluorine gas, argon, neon, and mixtures thereof. Corona treatment in air is most preferred.

Image Formation

When employing an inkjet printer loaded with inkjet inks, the image formation is typically performed in a manner whereby ink droplets are ejected from inkjet heads onto a print medium based on digital signals. Although both single-pass inkjet printing and multi-pass (i.e. scanning) inkjet printing may be used for image formation, single-pass inkjet printing is preferable as it is effective to perform high-speed printing. Single-pass inkjet printing is an inkjet printing method with which ink droplets are deposited onto the print medium to form all pixels of the image in a single passage of the print medium through the image forming device, i.e. beneath an inkjet marking module.

Referring to FIG. 1, after pre-treatment, the sheet S of print medium is conveyed on the transport belt 3 to an image forming device or inkjet marking module 9, where image formation is carried out by ejecting ink from inkjet marking device 91, 92, 93, 94 arranged so that a whole width of the sheet S is covered. That is, the image forming device 9 comprises an inkjet marking module having four inkjet marking devices 91, 92, 93, 94, each being configured and arranged to eject an ink of a different colour (e.g. Cyan, Magenta, Yellow and Black). Such an inkjet marking device 91, 92, 93, 94 for use in single-pass inkjet printing typically has a length corresponding to at least a width of a desired printing range R (i.e. indicated by the double-headed arrow on sheet S), with the printing range R being perpendicular to the media transport direction along the transport path P.

Figure 2:
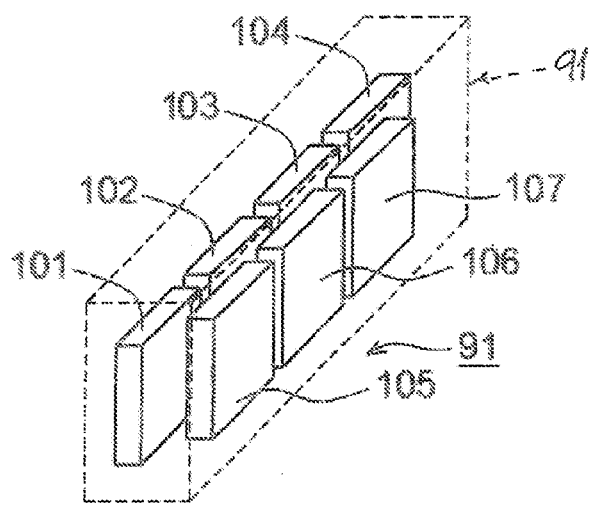
FIG. 2 is a schematic perspective view of an image forming device in the printing system of FIG. 1.
Figure 3A:
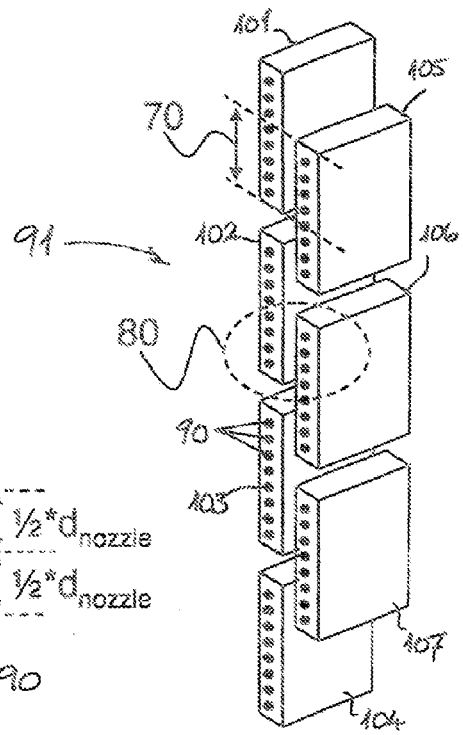
FIG. 3A is a schematic perspective underside view of printing heads in the image forming device of FIG. 2.
Figure 3B:
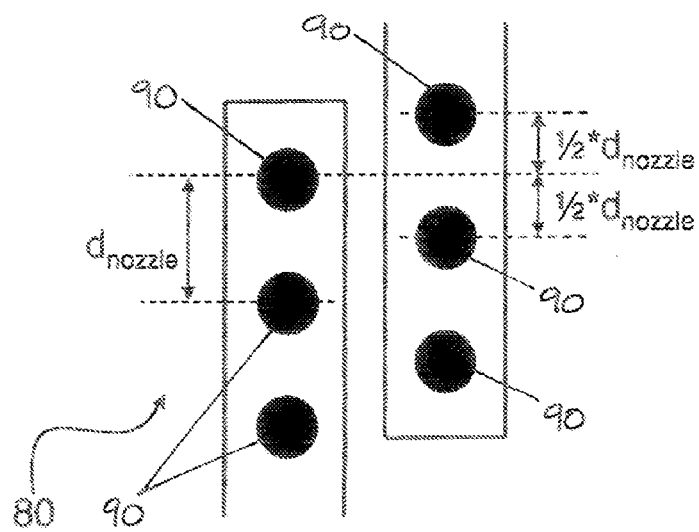
FIG. 3B is a detailed view of the printing heads in the image forming device of FIG. 2 and FIG. 3A.

Each inkjet marking device 91, 92, 93, 94 may have a single print head having a length corresponding to the desired printing range R. Alternatively, as shown in FIG. 2, the inkjet marking device 91 may be constructed by combining two or more inkjet heads or printing heads 101-107, such that a combined length of individual inkjet heads covers the entire width of the printing range R. Such a construction of the inkjet marking device 91 is termed a page wide array (PWA) of print heads. As shown in FIG. 2, the inkjet marking device 91 (and the others 92, 93, 94 may be identical) comprises seven individual inkjet heads 101-107 arranged in two parallel rows, with a first row having four inkjet heads 101-104 and a second row having three inkjet heads 105-107 arranged in a staggered configuration with respect to the inkjet heads 101-104 of the first row. The staggered arrangement provides a page-wide array of inkjet nozzles 90, which nozzles are substantially equidistant in the length direction of the inkjet marking device 91. The staggered configuration may also provide a redundancy of nozzles in an area O where the inkjet heads of the first row and the second row overlap. (See in FIG. 3A). The staggering of the nozzles 90 may further be used to decrease an effective nozzle pitch d (and hence to increase print resolution) in the length direction of the inkjet marking device 91. In particular, the inkjet heads are arranged such that positions of the nozzles 90 of the inkjet heads 105-107 in the second row are shifted in the length direction of the inkjet marking device 91 by half the nozzle pitch d, the nozzle pitch d being the distance between adjacent nozzles 90 in an inkjet head 101-107. (See FIG. 3B, which shows a detailed view of 80 in FIG. 3A). The nozzle pitch d of each head is, for example, about 360 dpi, where "dpi" indicates a number of dots per 2.54 cm (i.e. dots per inch). The resolution may be further increased by using more rows of inkjet heads, each of which are arranged such that the positions of the nozzles of each row are shifted in the length direction with respect to the positions of the nozzles of all other rows.

In the process of image formation by ejecting ink, an inkjet head or a printing head employed may be an on-demand type or a continuous type inkjet head. As an ink ejection system, an electrical-mechanical conversion system (e.g. a single-cavity type, a double-cavity type, a bender type, a piston type, a shear mode type, or a shared wall type) or an electrical-thermal conversion system (e.g. a thermal inkjet type, or a Bubble Jet® type) may be employed. Among them, it is preferable to use a piezo type inkjet recording head which has nozzles of a diameter of 30 μm or less in the current image forming method.

The image formation via the inkjet marking module 9 may optionally be carried out while the sheet S of print medium is temperature controlled. For this purpose, a temperature control device 10 may be arranged to control the temperature of the surface of the transport mechanism 2 (e.g. belt or drum 3) below the inkjet marking module 9. The temperature control device 10 may be used to control the surface temperature of the sheet S within a predetermined range, for example in the range of 30° C. to 60° C. The temperature control device 10 may comprise one or more heaters, e.g. radiation heaters, and/or a cooling means, for example a cold blast, in order to control and maintain the surface temperature of the print medium within the desired range. During and/or after printing, the print medium is conveyed or transported downstream through the inkjet marking module 9.

Drying and Fixing

After an image has been formed on the print medium, the printed ink must be dried and the image must be fixed on the print medium. Drying comprises evaporation of solvents, and particularly those solvents that have poor absorption characteristics with respect to the selected print medium.

FIG. 1 of the drawings schematically shows a drying and fixing unit 11, which may comprise one or more heater, for example a radiation heater. After an image has been formed on the print medium sheet S, the sheet S is conveyed to and passed through the drying and fixing unit 11. The ink on the sheet S is heated such that any solvent present in the printed image (e.g. to a large extent water) evaporates. The speed of evaporation, and hence the speed of drying, may be enhanced by increasing the air refresh rate in the drying and fixing unit 11. Simultaneously, film formation of the ink occurs, because the prints are heated to a temperature above the minimum film formation temperature (MFT). The residence time of the sheet S in the drying and fixing unit 11 and the temperature at which the drying and fixing unit 11 operates are optimized, such that when the sheet S leaves the drying and fixing unit 11 a dry and robust image has been obtained. As described above, the transport mechanism 2 in the fixing and drying unit 11 may be separate from the transport mechanism 2 of the pre-treatment and printing parts or sections of the printing system 1 and may comprise a belt or a drum.

Post Treatment

To improve or enhance the robustness of a printed image or other properties, such as gloss level, the sheet S may be post treated, which is an optional step in the printing process. For example, in a preferred embodiment, the printed sheets S may be post-treated by laminating the print image. That is, the post-treatment may include a step of applying (e.g. by jetting) a post-treatment liquid onto a surface of the coating layer, onto which the ink has been applied, so as to form a transparent protective layer over the printed recording medium. In the post-treatment step, the post-treatment liquid may be applied over the entire surface of an image on the print medium or it may be applied only to specific portions of the surface of an image. The method of applying the post-treatment liquid is not particularly limited, and may be selected from various methods depending on the type of the post-treatment liquid. However, the same method as used in coating the pre-treatment liquid or an inkjet printing method is preferable. Of these, an inkjet printing method is particularly preferable in view of: (i) avoiding contact between the printed image and the post-treatment liquid applicator; (ii) the construction of an inkjet recording apparatus used; and (iii) the storage stability of the post-treatment liquid. In the post-treatment step, a post-treatment liquid containing a transparent resin may be applied on the surface of a formed image so that a dry adhesion amount of the post-treatment liquid is 0.5 g/m² to 10 g/m², preferably 2 g/m² to 8 g/m², thereby to form a protective layer on the recording medium. If the dry adhesion amount is less than 0.5 g/m², little or no improvement in image quality (image density, colour saturation, glossiness and fixability) may be obtained. If the dry adhesion amount is greater than 10 g/m², on the other hand, this can be disadvantageous from the view-point of cost efficiency, because the dryness of the protective layer degrades and the effect of improving the image quality is saturated.

As a post-treatment liquid, an aqueous solution comprising components capable of forming a transparent protective layer over the print medium sheet S (e.g. a water-dispersible resin, a surfactant, water, and other additives as required) is preferably used. The water-dispersible resin in the post-treatment liquid preferably has a glass transition temperature (Tg) of −30° C. or higher, and more preferably in the range of −20° C. to 100° C. The minimum film forming temperature (MFT) of the water-dispersible resin is preferably 50° C. or lower, and more preferably 35° C. or lower. The water-dispersible resin is preferably radiation curable to improve the glossiness and fixability of the image. As the water-dispersible resin, for example, any one or more of an acrylic resin, a styrene-acrylic resin, a urethane resin, an acryl-silicone resin, a fluorine resin or the like, is preferably employed. The water-dispersible resin can be suitably selected from the same materials as that used for the inkjet ink. The amount of the water-dispersible resin contained, as a solid content, in the protective layer is preferably 1% by mass to 50% by mass. The surfactant used in the post-treatment liquid is not particularly limited and may be suitably selected from those used in the inkjet ink. Examples of the other components of the post-treatment liquid include antifungal agents, antifoaming agents, and pH adjustors.

Hitherto, the printing process was described such that the image formation step was performed in-line with the pre-treatment step (e.g. application of an (aqueous) pre-treatment liquid) and a drying and fixing step, all performed by the same apparatus, as shown in FIG. 1. However, the printing system 1 and the associated printing process are not restricted to the above-mentioned embodiment. A system and method are also contemplated in which two or more separate machines are interconnected through a transport mechanism 2, such as a belt conveyor 3, drum conveyor or a roller, and the step of applying a pre-treatment liquid, the (optional) step of drying a coating solution, the step of ejecting an inkjet ink to form an image and the step or drying an fixing the printed image are performed separately. Nevertheless, it is still preferable to carry out the image formation with the above defined in-line image forming method and printing system 1.

With reference now to FIG. 4 of the drawings, the inkjet printing system 1 according to the preferred embodiment of the invention is shown to include an apparatus 20 for detecting defects in the printing system 1, and particularly for identifying and for classifying deformations D in the sheets S of print medium when the sheets S are on the transport path P of the printing system 1. In this particular embodiment, the apparatus 20 comprises a sensing unit 21, which processes the sheets S on the transport path P before those sheets S enter the image forming device 9. In this regard, it will be noted that the printing system 1 in FIG. 4 has a transport path P which includes both a simplex path $P_S$ and a duplex path $P_D$ and the sensing unit 21 of the apparatus 20 is arranged such that sheets S input on the simplex path $P_S$ and also returning on the duplex path $P_D$ all pass via the sensing unit 21.

At least one first sensor device 22 in the form of an optical sensor, such as a laser scanner, is provided within the sensing unit 21 for sensing the surface geometry or topology of the sheets S as they travel on a first pass or a second pass along the transport path P. The laser scanner or optical sensor device 22 generates digital image data I of the three-dimensional surface geometry or topology of each sheet S sensed or scanned. When performing the sensing or measuring of the surface geometry or topology of the sheets S on the transport path P of printing system 1 with the first sensor device(s) 22, it is highly desirable for the purposes of accuracy and reliability that the sheets S are transported or conveyed in the sensing unit 21 in substantially the same manner as those sheets S are later transported in the image forming unit or marking module 9. To this end, the sensing unit 21 includes a sheet conveyor mechanism 23 that simulates the sheet transport conditions provided by the transport mechanism 3' within the image forming unit 9. In this regard, both the conveyor mechanism 23 and the transport mechanism 3' include a belt transport device with vacuum sheet-holding pressure, as seen in FIG. 4.

The sheet topology data from the first sensor device 22 is then transmitted (e.g. either via a cable connection or wirelessly) to a controller 24 which includes a processor device 25 for processing and analysing the digital image data I to detect and to classify any defect or deformation D in the surface geometry or topology of each sheet S sensed or scanned. The sensing unit 21 is thus arranged to scan the sheets S for detecting and measuring any deformations or defects D before the sheets S enter the image forming device or inkjet marking module 9. In this way, if the processor device 25 determines that a sheet S on the transport path P includes a defect or deformation D that would render the sheet unsuitable for printing, the controller 24 is configured to prevent the sheet S from progressing to the inkjet marking module 9. The sensing unit 21 comprising the first sensor device(s) 22 is therefore desirably provided as a separate sentry unit positioned on the transport path P sufficiently upstream of the marking module 9. The controller 24 and processor device 25 may be integrated within the sentry unit 21 or they may be separately or remotely located.

Referring also to FIG. 5, some additional elements of the printing system 1 and the apparatus 20 are illustrated. For example, located immediately downstream of the first sensor device 22 in the sentry unit 21 is an additional sheet conveyor 23' that rotates and translates each sheet S on the transport path P before the sheet S passes removal device 26. It will also be noted that the printing system 1 includes a sheet registration entry unit 3" for regulating a position or orientation of each sheet S on the transport path P as the sheet S enters the image forming device 9.

Processing of the Data

The digital data I representing the surface geometry or topology of each sheet S and comprising an array of image pixels is processed and analysed in processor device 25. In a first processing step, a binary image is created where each pixel exceeding a pre-set height threshold given by TOL is set to 1, all other pixels are set to 0. The minimum height threshold level for detecting defects is preferably set to 400 μm, as it has been found that a lower level results in detection of too many very small, non-relevant defects. The processor device 25 produces a height map for each sheet S. This height map is used to detect and measure or classify any defects present within the sheet, and particularly any out-of-plane deformations D, such as wrinkles, dog ears, curl, tears etc. In this embodiment, a defect is defined as a measurement point or pixel within the height map having at least 4 connected neighbours also exceeding a pre-set threshold value.

Figure 6:
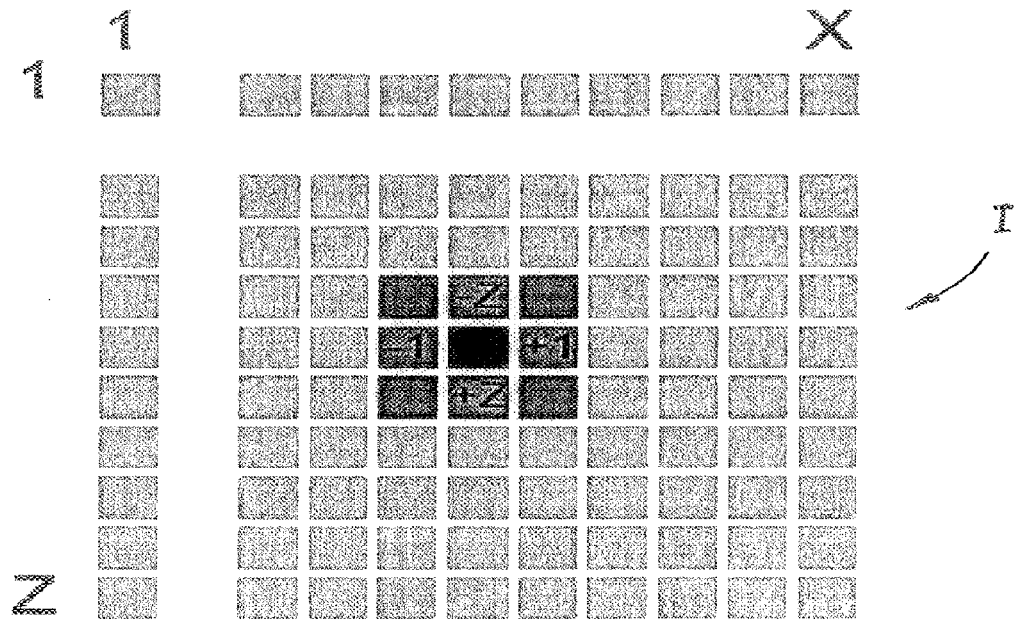
FIG. 6 is a schematic illustration of the analysis of an eight connected pixel neighbourhood in a preferred embodiment of the apparatus and method of the invention.

The defect analysis algorithm makes use of linear indexing for addressing the image content. This is convenient since all neighbour pixel locations can easily be determined by simply adding or subtracting a value from the current index. Each position in the image can be addressed as Image (i*Z+j) where i=1 . . . Z and j=1 . . . X. Addressing the four directly connected neighbours by offsets to the index is visualized in FIG. 6. Indeed, as shown in FIG. 6, an eight connected neighbourhood is used for the defect analysis or extraction, i.e. the corners are included. Thus, one of the steps in finding pixels that are part of the defect includes generating a pixel list of all neighbouring pixels of pixels known to form a part of the defect. As this algorithm can return the same index multiple times, however, it is desirable for this list of indices to be cleaned by removing all duplicate indices. This prevents unnecessary calculations and multiple inclusions of the same data, which would otherwise cause errors in the calculation of defect properties. The function used to determine whether a pixel forms part of the defect is combined within this filter step. The algorithm used for removing double entries uses a simple approach, which may not offer the highest performance. However, as the number of defects within a sheet S is limited and the number of pixels within a defect is usually small, this approach does not consume too much calculation time. Otherwise a filter function using a hash algorithm may offer higher performance.

Figure 7:
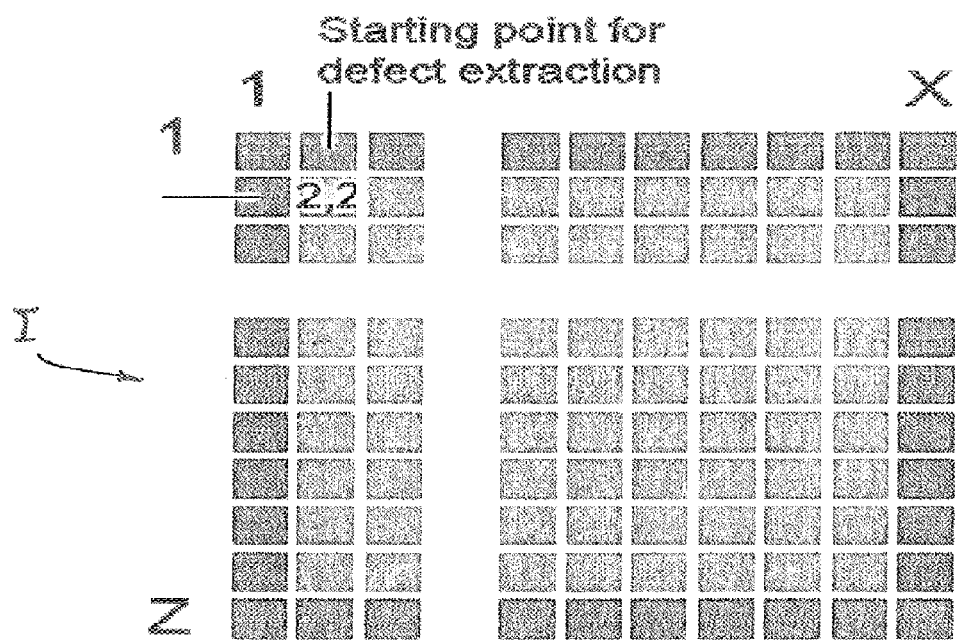
FIG. 7 is a schematic illustration of pixels on edges of the image data which are assigned a value below the defect threshold before the analysis process starts.

With reference to FIG. 7, the image pixels on the image edges are assigned a value below the defect threshold before the defect analysis process starts to prevent generation of invalid indices. The defect analysis or extraction thus starts at image element 2,2. By virtue of this value assignment, an image element on the edges of the height map will never be assigned to a defect area and the algorithm will never try to index its neighbours. Thus, in order to avoid defects D at an edge of the sheet S not being measured or classified correctly, the edge of the sheet S should not be located at the edge of the image. As an alternative the size of the image containing the height map could be increased along all sides by one pixel containing a value less than the threshold value for defect extraction.

Figure 8:
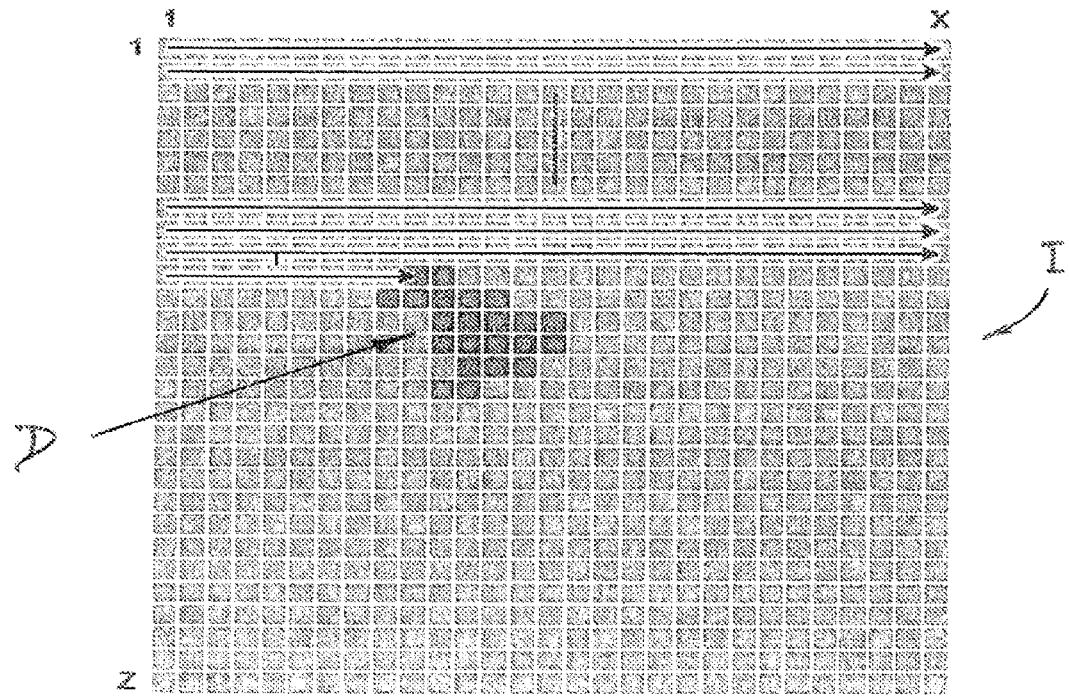
FIG. 8 is a schematic illustration of the image data in the embodiment of the apparatus and method of the invention being analysed by row major until a data pixel representing a deformation is found, at which point all of the pixel neighbours are assessed.
Figure 9:
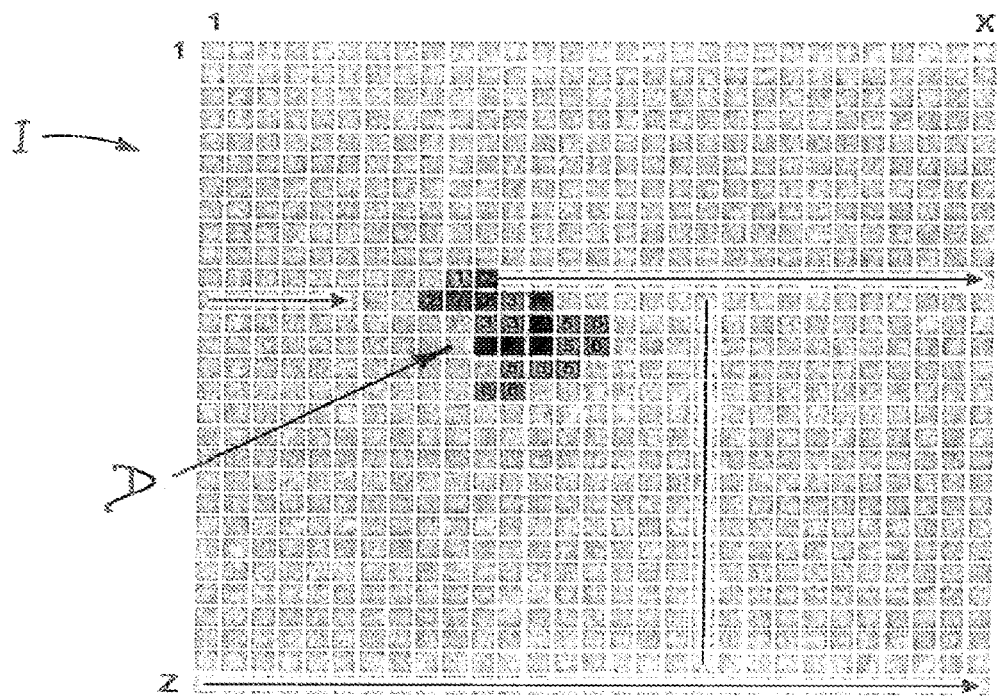
FIG. 9 is a schematic illustration of the image data in FIG. 8, with the pixel neighbours within the deformation analysed, the numbers indicating the iteration steps, and the analysis for new defects continuing when all pixels within the deformation have been found.

Referring to FIG. 8, the image pixel data I from the sensor device 22 is analysed by the processor 25 row-by-row or "row major" until a defect pixel is detected. Starting at this point, all immediately adjacent or neighbouring pixels are then tested to see if they belong to the defect, as shown in FIG. 9. The neighbouring pixels within the defect are tested, with the pixel numbering in FIG. 9 indicating the iteration steps. Further analysing the image pixel data I row-by-row for new defects then continues when all pixels within a defect or deformation D have been found. To perform a measurement and classification of a defect D and/or for later statistical analysis of the defects, the following defect properties are assessed:

Maximum Height: The highest point H within the defect
Defect Area, A: The area A is equal to the number of pixels that belong to the defect or deformation D, which is the sum of the unique pixels found during each iteration of the defect search algorithm.
Bounding Box, B: The bounding box is identified by the top left Z, X coordinates and width in both directions
Centre of Gravity, C:

$$C = \frac{1}{M}\sum_{i=1}^{n} m_i r_i$$

where M is the accumulated height (total mass) of the defect, $m_i$ is the height of individual pixels within the defect, and $r_i$ is the pixel coordinates (z, x)

Figure 10:
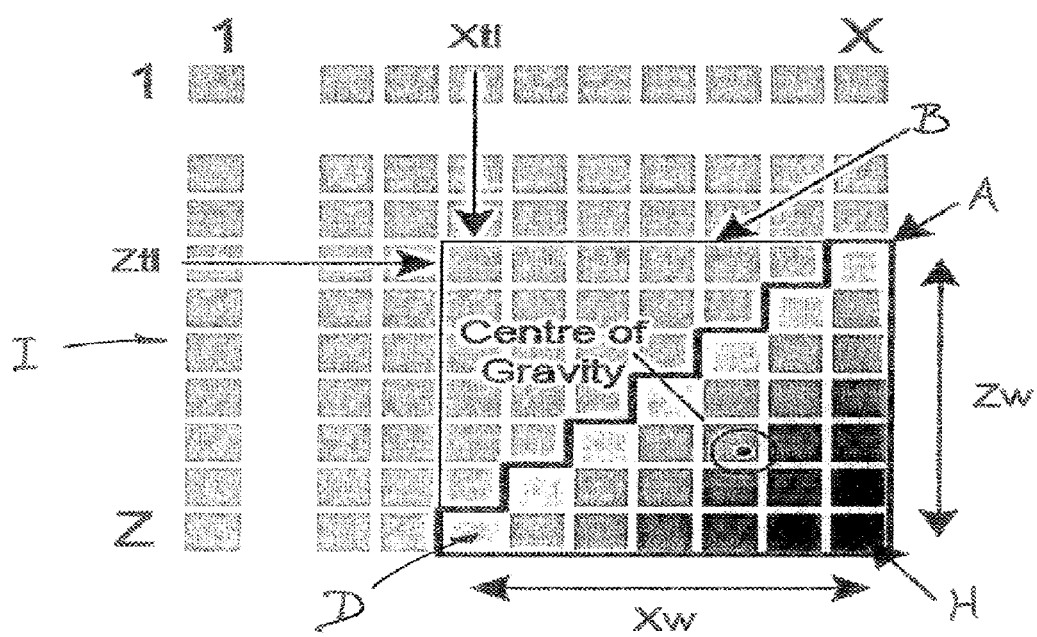
FIG. 10 is a schematic illustration of various properties for a dog-ear type of sheet deformation.

With reference to FIG. 10 of the drawings, the properties for a dog ear type of defect are illustrated. These properties for the dog-ear defect include: maximum height H located at corner of bounding box B, a centre of gravity C located near a diagonal of the bounding box B, and an area A of approximately 50% of bounding box area.

The defect properties belonging to the current defect being processed are updated each time a new list of neighbour pixels has been found. Since the properties are quite simple, the processing is straight-forward. The most 'complex' property is the centre-of-gravity C. During the defect extraction, the sum of the individual Z and X and total weights is calculated. After all pixels belonging to the defect have been found, the centre-of-gravity can be calculated from these three values. During the defect analysis or extraction process, the defect properties are determined for all defects found. When the analysis for a specific defect is finished, its characteristics can be used to determine whether the defect is to be included in the defect list or not. The characteristics for a maximum number of defects (e.g. 20) may be stored. Defects detected having an area of less than 10 pixels may be neglected as these are most likely just noise elements or the fringes of a real defect. Fringe defects are mainly caused by noise within the height map. Most fringe defect areas are smaller than 3 pixels. The largest fringe defect area may be 7 pixels in area. Thus, the defect area A will be used to report defects only when their area is equal to or greater than 10 pixels.

Another approach for the elimination of small defects may be to filter the image data I before defect analysis. There are several options for doing this, including:

(i) Removing all defects containing less than a predefined number of pixels. A drawback here is that a defect must first be identified, so performing this operation separately will consume more processing time.

(ii) Performing a dilation operation before defect detection. This can help to 'remove' small fringe defects. Such fringe defects are merged into a larger defect.

(iii) Performing an erosion operation before defect analysis or detection. This can remove small defects. The maximum size of the defects that will effectively be removed is determined by the size and shape of the erosion kernel. It is not yet clear if the small fringe type defects will be removed. The larger the filter kernel the more processing time is needed.

Print System Control

With reference again to FIGS. 4 and 5, after the image data I has been analysed by the processor 25 and the defects or deformations D within the sheet S have been extract and classified accordingly, the controller 24 may transmit a control signal (e.g. either via cable or wirelessly) to a removal device or ejector device 26 for regulating the transport or conveyance of the sheets S to the image forming device or inkjet marking module 9. In particular, if the sheet S has been determined by the processor 25 to include one or more deformations D with a size or extent above a predetermined threshold sufficient to render the sheet unsuitable for printing, the controller 24 is configured to control or operate the removal device 26 to remove or eject the sheet S from the transport path P to a reject tray 27. The controller 24 controls sheet removal or rejection via the removal device 26 on the basis of a sheet form detection result from the processor device 25 compared with at least one predetermined rejection criterion. This rejection criterion is typically defined by a maximum allowable height H of a detected deformation D out of the plane of the sheet S because in an inkjet printing system 1 the passage of the sheet S through the narrow print gap under the printing heads 101-107 is most critical. In particular, while a larger print gap in inkjet applications provides robustness against sheet deformations or sheet jams, it results in a lower print quality, so the print gap is often kept as small as practicable.

In this way, sheet jams within the print module or image forming device 9 may be avoided when sheets S are found to contain too much deformation. The removal device 26 located between the sentry unit 21 and the inkjet marking module 9 can employ different means optimized for redirecting the sheets S from the transport path P towards the reject tray 27. In this particular embodiment, rollers are used. In principle, control of the removal device or ejector device 26 by the controller 24 can be based solely upon one predetermined criterion to perform its job, such as a maximum allowable deformation height or size. However, information gathered on deformation of the sheet S may also be used for statistical purposes to determine media run-ability. For statistical purposes more information is generally useful, such as a number of the deformed areas or defects D present within a sheet S, the area A of each defect D, etc. The classification data may be stored in, and later retrieved from, the controller 24 for further analysis. The predetermined rejection criterion in the apparatus 20 is varied depending on the operating parameters or conditions of the printing system 1, e.g. one or more of: a material of the sheet S; an operating mode of the printing system (e.g. a high productivity mode or a high print-quality mode); a position of the deformation D on the sheet S (e.g. leading edge, trailing edge, middle of sheet), a shape or type of the deformation D (e.g. a dog-ear, waviness, or a curl), and/or whether the sheet S is on a simplex pass or a duplex pass of the transport path P.

In this regard, the impact of removing or ejecting a sheet S on the duplex pass is often higher than removing or rejecting the sheet S on the simplex pass because sheet removal on the duplex pass results in a missing page in the output, and duplex sheets following a removed or rejected sheet also need to be removed to ensure that the printed images are in the correct order in the final output. Thus, it is possible that the printing system 1 may have different modes of operation, such as a high-productivity mode (e.g. with higher rejection threshold criterion on the duplex pass) or a high-print-quality mode (e.g. with lower rejection threshold criterion on the duplex pass). Also, the likelihood of sheet damage or deformation occurring on the duplex pass typically depends on the material or print medium of the sheet, so here again it is possible to set a unique simplex and duplex threshold for each material or print medium type. In addition, it is possible to vary the predetermined criterion based on defect location within the sheet S (e.g. leading edge, trailing edge, middle of sheet), or based on the type of defect (e.g. dog-ear, waviness, or curl). In this regard, it will be noted that a higher threshold criterion for trailing edge defects and/or for waviness on a side edge of the sheet S may be tolerated because these are less likely to cause a sheet jam. Thus, unlike prior art systems in which the same rejection criterion is applied regardless of the printing application or printing parameters, the system of the present invention is able to be optimized according to variable applications and requirements. In other words, having one or more variable criteria provides a system which is adaptable depending on the application.

At least one second sensor 28 for sensing the surface geometry or topology of the sheet S located within the image forming unit 9 can be used to provide feedback or correlation data I' to the sentry unit 21 or to the controller 24 to increase the accuracy of the measurement of the sheet deformation D. Various parameters affecting the simulated transport conditions via the sheet conveyor mechanism 23 in the sentry unit 21 can be changed using this feedback signal to optimize the prediction result. Several sensing or measurement techniques can be used to sense or measure sheet deformation D. A two-dimensional (2D) laser triangulation sensor can create a three-dimensional (3D) sheet image when the sheet S passes the first and/or second sensor devices 22, 28. The second sensor device 28 used to provide feedback data does not necessarily need to be identical to the first sensor device 22 used within the sentry unit 21. A one-dimensional (1D) sheet height sensor using a collimated light sheet can be used to measure the sheet profile perpendicular to the direction of travel along the transport path P. In addition to improving the accuracy of the sensing unit 21, the feedback system via the second sensor device(s) 28 can be used for optimizing system productivity. In this regard, too many sheets will be rejected if the pre-set defect criteria are too sensitive, while too much print quality degradation and/or too many sheet jams will occur if the pre-set defect criteria are not sensitive enough. Accordingly, the sheet rejection threshold can be optimized using the second measurement on the print belt 3', especially in situations where the sheet deformation D changes between sentry unit 21 and image forming unit 9.

Figure 11:
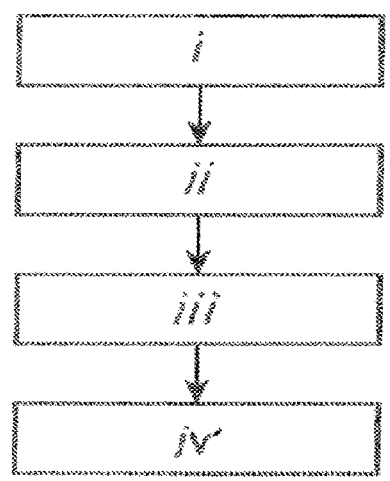
FIG. 11 is a flow diagram which schematically illustrates a method according to a preferred embodiment.

Referring now to FIG. 11 of the drawings, a flow diagram is shown that schematically illustrates the steps in a method of detecting defects in a printing system 1 according to the preferred embodiment of the invention described above with respect to FIGS. 1 to 9. In this regard, the first box i of FIG. 10 represents the step of feeding or conveying a sheet S of paper or another print medium along a transport path P of the printing system 1. The second box ii represents the step of sensing a surface geometry or a topology of the sheet of print medium via a first sensing device 22 (e.g. a laser scanner) as the sheet S travels along the transport path P to generate image data I which is representative of that surface geometry or topology. The third box iii then represents the step of processing the surface geometry or topology data I generated in the sensing step according to at least one predetermined criterion to detect and classify deformations D in the surface geometry or topology of the sheet S, e.g. using the processor device 25. In this regard, the at least one predetermined criterion typically comprises one or more of a height H of the deformation D out of a plane of the sheet S, and an area A of the deformation D in the plane of the sheet S. The final box iv in drawing FIG. 11 then represents the step of selecting or adjusting the at least one predetermined criterion in the processing step depending upon conditions or parameters of the printing system 1, particularly on one or more of: whether the sheet S is on a simplex pass or a duplex pass of the transport path P; a material of the sheet S to be printed; an operating mode of the printing system 1; a position of a detected deformation D on the sheet S; and/or a shape or type of a detected deformation D. The method will then typically include controlling the further progress of the sheet S along the transport path P of the printing system 1 depending upon the deformations D in the surface geometry or topology of the sheet detected and classified in the processing step. That is, if the processor 25 determines that one or more of the deformations D detected and classified render the sheet S unsuitable for printing, the controlling step includes effecting removal of the sheet S from the transport path P to prevent the sheet progressing to the inkjet marking module 9. On the other hand, if the processor device 25 does not detect any relevant deformation D that would render the sheet S unsuitable for printing, the controller 24 then permits the sheet S to progress on the transport path P to the inkjet marking module 9.

Figure 12:
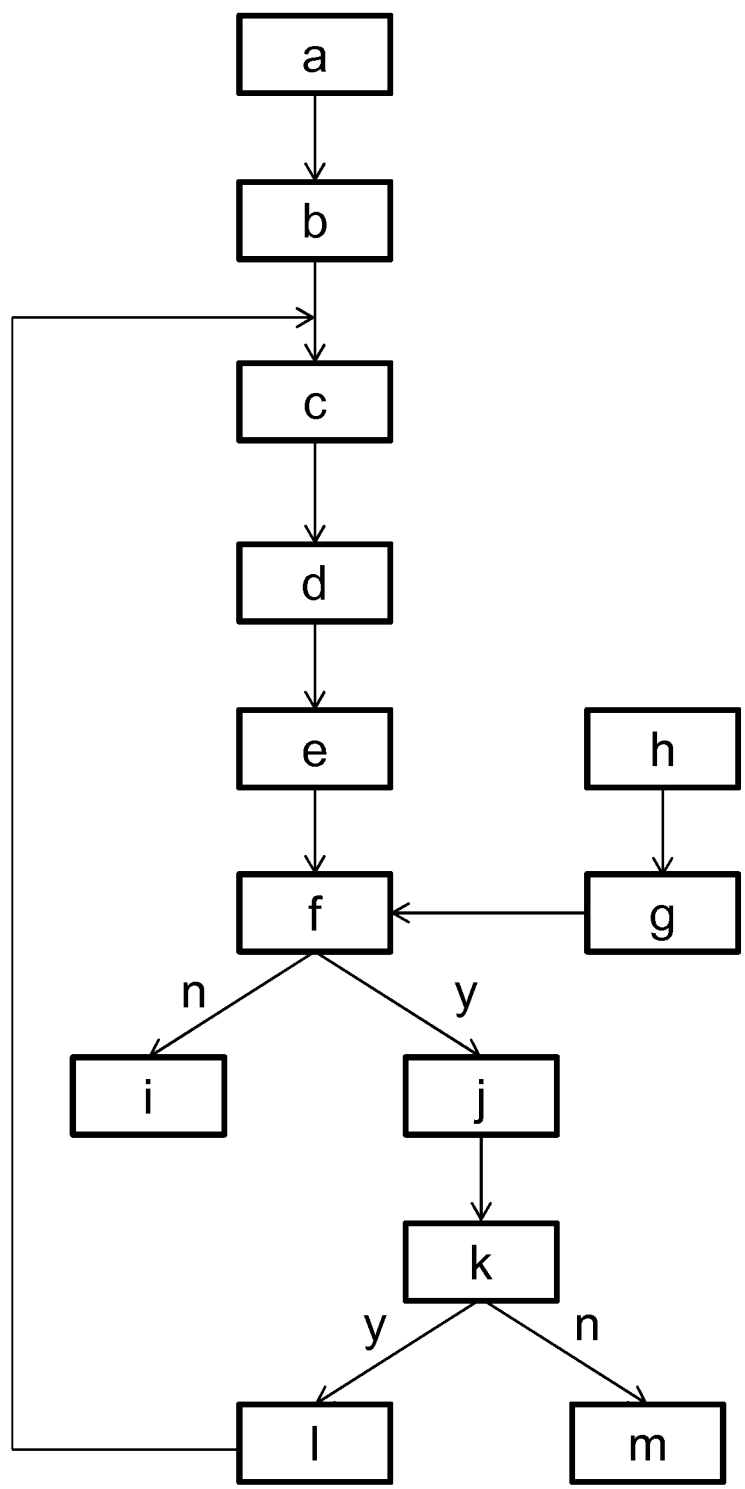
FIG. 12 is a flow diagram which schematically illustrates a method according to a further embodiment.

Finally, referring now to FIG. 12, a flow diagram of an embodiment of a method according to the present invention is illustrated. In step a, a print job with predefined job settings is started and a sheet S is inserted into the printing system 1, for example from a sheet input module. In the optional step b, the sheet S is treated prior to printing said sheet S, for example by exposing the sheet S to a predetermined temperature or humidity. The sheet S is the transported along the transport path to the sensing unit 21 (sentry unit 21). Prior to step a, there may be a step for inputting the job settings into the printing system, for example via an input module or user interface.

In step c, the surface of the sheet S is sensed by the sensing unit 21. The sheet S is scanned by a sensing unit 22, which generates data I representing a height map of the sensed surface of the sheet S. Preferably, the height map data I corresponds to the majority of the sheet's S surface or to complete surface of the sheet S. The data I is then sent to the processor device 25 for analysis.

In step d, the processor device 25 detects deformations in the surface of the sensed sheet S by analyzing the data I for said sheet S. Preferably, the processor device 25 determines a plurality of properties for each deformation or defect, such as position on the sheet, maximum height, area, bounding box surface, and/or other relevant defect-related parameters.

In the optional step e, the processor device 25 classifies the deformations based on their properties determined in step d. For example, the processor device 25 is arranged to distinguish between different deformation types or classes, and can classify the detected deformation accordingly. The processor device 25 may be arranged for classifying the detected deformations into deformation classes by comparing the determined properties for each detected deformations to a classification database. The database may comprise a range for each property of a class, such that deformations may be classed by comparing the determined values for the properties of a deformation to the at least one range of a deformation class.

In step f, the data I is compared to a reference to determine whether the sheet is suitable for printing. Specifically, the properties determined in step d may be compared to references. For example, the maximum of height of each deformation detected in the sheet is compared to the print head gap spacing, and a sheet is deemed unsuitable for printing when a maximum height exceeds the print head gap spacing to avoid "head touch". Specifically, when a determined property of a detected deformation of a sheet S exceeds a reference for that property, the sheet S is identified as unsuitable for printing. The reference may alternatively comprise a range for a respective property, and when the processor device 25 determines that a value for the respective property lies outside said range, the processor device 25 identifies the sheet as unsuited for printing. At least one property of at least one detected deformation is compared to the reference to determine a sheet's suitability for printing. To increase accuracy, a plurality of thresholds may be applied for a plurality of relevant properties.

In step g, the reference is to which a respective is compared is selected or provided. The reference is selectable or adjustable based on at least one job parameter which job parameter is determined in step h. In step h, the job parameter is based on or determined by the print job settings which started the print job in step a. When the job parameter provided in step h is changed, the at least one corresponding reference in step g may be changed accordingly. Basically, the reference provided in step g, provides a criterion for the printing suitability of a sheet. The criterion can be selected or adjusted based on the job parameter.

For example, the job parameter is an operating mode, selectable or adjustable between high productivity mode and low productivity mode. When the operating mode is changed from low productivity mode to high productivity mode, one or more references are increased, such that the rejection criteria become less constrained. In this manner less sheets are rejected, increasing productivity. In another example the job parameter is printing mode, changeable between simplex and duplex. The thresholds for duplex printing may be set larger than for simplex printing, since the impact of ejecting a to be duplex printed sheet S has a greater impact on productivity than the ejection of a to be simplex printed sheet S. In a further example, the job parameter is deformation position on the sheet S, alternating between e.g. at the leading edge, at the trailing edge, and/or at the center of the sheet. Thresholds may be lowered when a deformation is detected at the leading edge of the sheet S with respect to the thresholds applied when the same deformation would be positioned at the trailing edge or centre of the sheet. This is convenient since a defect at the leading edge has an increased change of causing paper jams compared to deformations at the trailing edge or centre of the sheet S.

In step h, the job parameter is determined. The job parameter may be determined by the job settings provided in step a, either based on input from the processor device 25 or via a user interface. For example, the user interface may allow the user to select for example between high and low productivity modes or different material types for the sheet when inputting the print job with its job settings. Alternatively, the processor device 25 provides for example sheet related information, such as the position of the detected deformation on the sheet or simplex-duplex pass information.

In step f, the processor device 25 identifies whether the sheet S is suitable for printing. If the answer is no, the sheet is deemed unsuitable for printing, and step i is performed. In step i, the sheet is ejected from the transport path of the printing system, either manually or via an ejector device 26 controllable by the processor device 25.

When in step f, the sheet S is deemed suited for printing, step j is executed. In step j, the sheet S is printed in the image forming unit. This can be done without the risk of "head touch" since the sheet S has been sensed by sensing unit 21 and checked by the processor device 25. After printing, the sheet S may be dried.

It is then determined in step k whether the sheet S is intended for duplex printing. If not, then step m is executed and the sheet S is output by the printing system, for example into a stacking device.

When in step k, the sheet S is intended for duplex printing, it is flipped in step I and transported back to the sensing unit 21, where upon at least steps c to f are performed for the flipped sheet S.

Although specific embodiments of the invention are illustrated and described herein, it will be appreciated by those of ordinary skill in the art that a variety of alternate and/or equivalent implementations exist. It should be appreciated that the exemplary embodiment or exemplary embodiments are examples only and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that in this document the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

The invention claimed is:

1. A method of detecting defects in a printing system, wherein a print job is started by an operator by inputting job settings into the printing system, which job settings comprise settings related to operating conditions of the printing system, the printing system comprising a controller performing the steps of:
   the job settings defining the operating conditions of the printing system, to which operating conditions a sheet is exposed in the printing system during an execution of the print job;
   monitoring a job parameter corresponding to at least one operating condition of the printing system during the execution of the print job;
   selecting a reference depending on the job parameter to suit the operating conditions in the printing system, which step of selecting the reference is triggered by the job parameter;
   sensing a surface geometry of the sheet to be printed on a transport path of the printing system to generate data representative of that surface geometry;
   processing the data generated to detect deformations in the surface geometry of the sheet; and
   determining the suitability for printing of the sheet by comparing the data of the sheet to the selected reference.

2. The method according to claim 1, wherein the triggering of selecting the reference comprises adjusting the reference when a change in the job parameter is determined.

3. The method according to claim 1, wherein the step of the controller monitoring the at least operating condition further comprises the controller providing sheet related information to determine the job parameter.

4. The method according to claim 1, wherein the reference provides at least one rejection criterion for a sheet on the transport path of the printing system, and wherein, when the operating conditions in the printing system vary, the at least one rejection criterion is modified depending on the operating conditions.

5. The method according to claim 4, wherein the at least on rejection criterion is selectable depending on at least one of the following:
   a material of the sheet to be printed;
   an operating mode of the printing system;
   a position of a deformation on the sheet;
   a shape or type of a deformation; and/or
   whether the sheet is on a simplex pass or a duplex of the transport path.

6. The method according to claim 1, wherein the step of the controller selecting the reference further comprises the controller adjusting the reference from one of at least two reference values to the other of the at least two reference values when the job parameter is changed, wherein each reference value corresponds to a value of a job parameter.

7. The method according to claim 1, wherein the step of the controller determining the job parameter comprises the controller determining at least one of the following:
   a sheet transport velocity;
   a sheet position in the printing system;
   a position of a detected deformation on the sheet; and
   a class of a detected deformation.

8. The method according to claim 1, further comprising controlling further progress of the sheet along the transport path of the printing system depending on the deformations identified and classified in the surface geometry of the sheet, including controlling or effecting removal of the sheet from the transport path of the printing system if one or more deformations detected would render the sheet unsuitable for printing.

9. The method according to claim 1, wherein the step of sensing the surface geometry of the sheet includes holding and conveying the sheet on the transport path in a manner substantially identical to a manner of holding and conveying the sheet in an image forming unit or printing head unit of the printing system; and/or
   wherein the step of sensing the surface geometry of the sheet takes place on a first pass or simplex pass of the transport path towards an image forming unit or a printing head unit of the printing system, and/or on a second pass or a duplex pass of the transport path towards the image forming unit or printing head unit of the printing system; and/or
   wherein the step of sensing the surface geometry of the sheet includes sensing substantially an entire surface or an entire side of the sheet, wherein the surface area or topology data includes image data comprising pixels.

10. The method according to claim 1, wherein the job parameter is selectable between:
    a simplex setting wherein a sheet is on a simplex pass for printing an image on a first side of the sheet; and
    a duplex setting wherein a sheet is on a duplex pass for printing a second image on a second side of the sheet, such that different rejection criteria are applied to the sheet on its duplex pass before printing the second image on its second side with respect to the same sheet on its simplex pass before printing the first image on its first side.

11. A printing system comprising:
an input module which allows an operator to input job settings to the printing system, which job settings comprise settings comprise settings related to operating conditions of the printing system, wherein a sheet is exposed to said operating conditions in the printing system during an execution of the print job;
a controller arranged for:
defining the operating conditions in the printing system from the job settings;
monitoring a job parameter, which job parameter corresponds to at least one operating condition during the execution of the print job;
selecting a reference depending on the job parameter to suit the operation conditions in the printing system, which step of selecting the reference is triggered by the job parameter; and
an apparatus for detecting defects in the printing system, the apparatus comprises:
a sensing unit comprising a first sensor device for sensing a surface geometry of a sheet to be printed as the sheet travels on a transport path of the printing system and for generating data representative of that surface geometry;
a processor device for processing the data from the first sensor device configured to detect deformations in the sheet and to determine whether a detected deformation renders the sheet unsuitable for printing by comparing a detected deformation to the selected reference.

12. The printing system according to claim 11, wherein the controller, for monitoring the job parameter, is arranged for determining at least one of the following:
a sheet transport velocity;
a sheet position in the printing system;
a position of a detected deformation on the sheet; and
a class of a detected deformation.

13. The printing system according to claim 11, wherein the controller is arranged for adjusting the reference from a first predefined reference to second predefined reference upon detection of a change in the job parameter.

14. The printing system according to claim 13, wherein the transport path comprises a simplex pass and a duplex pass, and wherein the controller is configured to select a different reference for a sheet on the duplex pass compared to a reference selected for a sheet on the simplex pass.

15. The printing system according to claim 14, wherein the controller is arranged for selecting the job parameter between:
a simplex setting wherein a sheet is on a simplex pass for printing an image on a first side of the sheet; and
a duplex setting wherein a sheet is on a duplex pass for printing a second image on a second side of the sheet, such that different rejection criteria are applied to the sheet on its duplex pass before printing the second image on its second side with respect to the same sheet on its simplex pass before printing the first image on its first side.

16. The printing system according to claim 11, further comprising a controller for controlling further progress of the sheet along the transport path of the printing system depending on deformations in the surface geometry of the sheet detected and classified by the processor device, wherein the controller is configured to control and/or operate a removal device for removing the sheet from the transport path of the printing system if the processor device detects one or more deformations in the surface geometry of the sheet that would render the sheet unsuitable for printing.

17. The printing system according to claim 11, wherein the sensor unit is configured and arranged to sense the surface geometry or topology of the sheet when the sheet is on a first pass or simplex pass of the transport path towards an image forming unit or a printing head unit of the printing system; and/or wherein the sensing unit is configured and arranged to sense the surface geometry of the sheet when the sheet is on a second pass or a duplex pass of the transport path towards the image forming or printing head unit of the printing system;
the sensing unit including a conveyor mechanism which is configured to hold and transport the sheet on the transport path in a manner substantially identical to a transport mechanism in an image forming unit or printing head unit of the printing system.

18. An apparatus for detecting defects in the printing system according to claim 11, which apparatus comprises:
a sensing unit comprising a first sensor device for sensing a surface geometry of a sheet to be printed as the sheet travels on a transport path of the printing system and for generating data representative of that surface geometry;
a processor device for processing the data from the first sensor device configured to detect deformations in the sheet and to determine whether a detected deformation renders the sheet unsuitable for printing by comparing a detected deformation to a reference;
a controller for selecting the reference based on a job parameter determined by the print job.

19. A method of detecting defects in a printing system, the method comprising the steps of:
initiating a print job on the printing system based on predefined job settings, wherein the print job determines a job parameter;
sensing a surface geometry of a sheet to printed on a transport path of the sheet in the printing system to generate data representative of that surface geometry;
processing the data generated to detect deformations in the surface geometry of the sheet;
determining the suitability for printing of the sheet by comparing the data of the sheet to a reference;
wherein the method further comprises the step of selecting the reference based on the job parameter;
wherein the step of processing the surface geometry data comprises applying at least one algorithm to the surface geometry data, the algorithm being configured to analyze pixels of the data according to at least one criterion, such as height, to identify and classify deformation in the sheet; and
wherein the algorithm is configured to analyze neighboring pixels of a pixel within a deformation.

* * * * *